(12) United States Patent
Brody et al.

(10) Patent No.: US 8,716,023 B2
(45) Date of Patent: May 6, 2014

(54) METHODS FOR ELIMINATING OR REDUCING THE EXPRESSION OF A GENES IN A FILAMENTOUS FUNGAL STRAINS

(75) Inventors: Howard Brody, Davis, CA (US); Suchindra Maiyuran, Gold River, CA (US); Hiroaki Udagawa, Yokohama (JP)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 1127 days.

(21) Appl. No.: 11/009,890

(22) Filed: Dec. 9, 2004

(65) Prior Publication Data

US 2005/0158844 A1 Jul. 21, 2005

Related U.S. Application Data

(60) Provisional application No. 60/528,367, filed on Dec. 9, 2003.

(51) Int. Cl.
*C12N 1/00* (2006.01)
*C12N 15/74* (2006.01)

(52) U.S. Cl.
USPC ..................... 435/471; 435/254.3; 435/254.6

(58) Field of Classification Search
USPC .......................... 435/254.3, 254.6, 471, 24.5
See application file for complete search history.

(56) References Cited

U.S. PATENT DOCUMENTS

2005/0013855 A1* 1/2005 Gould-Fogerite et al. .... 424/450

FOREIGN PATENT DOCUMENTS

| WO | WO 98/53083 | 11/1998 |
| WO | WO 01/49844 | 7/2001 |
| WO | WO 03/050288 | 7/2003 |
| WO | WO2005/026356 | 3/2005 |

OTHER PUBLICATIONS

Wiebe (2003, Mycologist. vol. 17: 140-144).*
Kadotani, Naoki et al., RNA Silencing in the Phytopathogenic Fungus *Magnaporthe otyzae*, MPMI, vol. 16, No. 9, 2003, pp. 769-776.
Cogoni, Carlo et al., Gene silencing in *Neurospora crassa* requires a protein homologous to RNA-dependent RNA polymerase, Nature, vol. 399, May 13, 1999, pp. 166-169.
Liu, Hong et al., RNA Interference in the Pathogenic Fungus *Cryptococcus neoformans*, Genetics, vol. 160, Feb. 2002, pp. 463-470.
Selker, 1997, *Trends Genet.* 13: 296-301.
Matzke and Matzke, 1998, *Cell. Mol. Life. Sci.* 54: 94-103.
Morel et al, 2000, *Curr. Biol.* 10: 1591-4.
Grewal and Moazed, 2003, *Science* 301: 798-802.
Hammond and Baulcombe, 1996, *Plant Mol. Biol.* 32: 79-88.
Xi-Song Ke et al., 2003, *Current Opinion in Chemical Biology* 7: 516-523.
Bernstein et al,. 2001, *Nature* 409: 363.
Elbashir et al., 2001, *Nature* 411: 494.
Elbashir et al, 2001, *Genes and Dev.* 15: 188.
Nykanen etal., 2001, *Cell* 197: 300.
Hammond et al., 2001, *Science* 293: 1146.
Kennerdell et al., 2000, *Nat. Biotechnol.* 18: 896-8.
Bosher et al., 1999, *Genetics* 153: 1245-56.
Voorhoeve and Agami, 2003, *Trends Biotechnol.* 21: 2-4.
McCaffrey et al., 2003, *Nat. Blotechnol.* 21: 639-44.
Hannon, 2002, *Nature* 418: 244-251.
Sharp et al., RNA Interference, Genes and Development, 2001, v. 15, part 5, pp. 485-490.
Hammond et al., Use of RNAI and a model system, Phytapathology, 2003, v. 93, part 6, p. S97.
Moyna et al., Gene silencing with RNA interference, Ferns Microbiology letters, 2004, v. 237, part 2, pp. 317-324.
Kadotani, Naoki et al., One of the Two Dicer-like Proteins in the Filamentous Fungi *Magnaporthe oryzae* Genome is Responsible for Hairpin RNA-triggered RNA Silencing and Related Small Interfering RNA Accumulation, The Journal of Biological Chemistry, vol. 279, No. 43, Issue of Oct. 22, 2004, pp. 44467-44474.

* cited by examiner

*Primary Examiner* — Jon E Angell
(74) *Attorney, Agent, or Firm* — Robert L. Starnes

(57) ABSTRACT

The present invention relates to methods for reducing or eliminating the expression of a target gene in a filamentous fungal strain, comprising: (a) inserting into the genome of the filamentous fungal strain a double-stranded transcribable nucleic acid construct comprising a first nucleotide sequence comprising a promoter operably linked to a homologous coding region of the target gene and a second nucleotide sequence comprising the homologous coding region, or a portion thereof, of the target gene, wherein the first and second nucleotide sequences are complementary to each other and the second nucleotide sequence is in reverse orientation relative to the first nucleotide sequence; and (b) inducing production of an interfering RNA encoded by the double-stranded transcribable nucleic acid construct by cultivating the filamentous fungal strain under conditions conducive for production of the interfering RNA; wherein the interfering RNA interacts with RNA transcripts of the target gene to reduce or eliminate expression of the target gene. The present invention also relates to the filamentous fungal strains and to methods of producing a biological substance of interest in such filamentous fungal strains.

14 Claims, 17 Drawing Sheets

SEQUENCE LISTING

<160> NUMBER OF SEQ ID NOS: 45

<210> SEQ ID NO 1
<211> LENGTH: 22
<212> TYPE: DNA
<213> ORGANISM: Aspergillus nidulens

<400> SEQUENCE: 1
gtgccccatg atacgcctcc gg                                              22

<210> SEQ ID NO 2
<211> LENGTH: 26
<212> TYPE: DNA
<213> ORGANISM: Aspergillus nidulens

<400> SEQUENCE: 2
gagtcgtatt tccaaggctc ctgacc                                          26

<210> SEQ ID NO 3
<211> LENGTH: 24
<212> TYPE: DNA
<213> ORGANISM: Aspergillus nidulens

<400> SEQUENCE: 3
ggaggccatg aagtggacca acgg                                            24

<210> SEQ ID NO 4
<211> LENGTH: 45
<212> TYPE: DNA
<213> ORGANISM: Aspergillus niger

<400> SEQUENCE: 4
caccgtgaaa gccatgctct ttccttcgtg tagaagacca gacag                     45

<210> SEQ ID NO 5
<211> LENGTH: 45
<212> TYPE: DNA
<213> ORGANISM: Aspergillus niger

<400> SEQUENCE: 5
ctggtcttct acacgaagga aagagcatgg ctttcacggt gtctg                     45

<210> SEQ ID NO 6
<211> LENGTH: 44
<212> TYPE: DNA
<213> ORGANISM: Aspergillus niger

<400> SEQUENCE: 6
ctatatacac aactggattt accatgggcc cgcggccgca gatc                      44

<210> SEQ ID NO 7
<211> LENGTH: 44
<212> TYPE: DNA
<213> ORGANISM: Aspergillus niger

<400> SEQUENCE: 7
gatctgcggc cgcgggccca tggtaaatcc agttgtgtat atag                      44

<210> SEQ ID NO 8
<211> LENGTH: 29
<212> TYPE: DNA
<213> ORGANISM: Trichoderma reesei

```
<400> SEQUENCE: 8
aacgttaatt aaggaatcgt tttgtgttt                              29

<210> SEQ ID NO 9
<211> LENGTH: 29
<212> TYPE: DNA
<213> ORGANISM: Trichoderma reesei

<400> SEQUENCE: 9
agtactagta gctccgtggc gaaagcctg                              29

<210> SEQ ID NO 10
<211> LENGTH: 26
<212> TYPE: DNA
<213> ORGANISM: Trichoderma reesei

<400> SEQUENCE: 10
actagtcgac cgaatgtagg attgtt                                 26

<210> SEQ ID NO 11
<211> LENGTH: 19
<212> TYPE: DNA
<213> ORGANISM: Trichoderma reesei

<400> SEQUENCE: 11
tgaccatggt gcgcagtcc                                         19

<210> SEQ ID NO 12
<211> LENGTH: 26
<212> TYPE: DNA
<213> ORGANISM: Trichoderma reesei

<400> SEQUENCE: 12
cgatcgtctc cctatgggtc attacc                                 26

<210> SEQ ID NO 13
<211> LENGTH: 28
<212> TYPE: DNA
<213> ORGANISM: Trichoderma reesei

<400> SEQUENCE: 13
actagttaat taagctccgt ggcgaaag                               28

<210> SEQ ID NO 14
<211> LENGTH: 20
<212> TYPE: DNA
<213> ORGANISM: Escherichia coli

<400> SEQUENCE: 14
taatacgact cactataggg                                        20

<210> SEQ ID NO 15
<211> LENGTH: 1416
<212> TYPE: DNA
<213> ORGANISM: Trichoderma reesei

<400> SEQUENCE: 15
atgattgtcg gcattctcac cacgctggct acgctggcca cactcgcagc tagtgtgcct    60
ctagaggagc ggcaagcttg ctcaagcgtc tggggccaat gtggtggcca gaattggtcg   120
ggtccgactt gctgtgcttc cggaagcaca tgcgtctact ccaacgacta ttactcccag   180
tgtcttcccg gcgctgcaag ctcaagctcg tccacgcgcg ccgcgtcgac gacttctcga   240
```

-continued

```
gtatccccca caacatcccg gtcgagctcc gcgacgcctc cacctggttc tactactacc    300
agagtacctc cagtcggatc gggaaccgct acgtattcag gcaacccttt tgttggggtc    360
actccttggg ccaatgcata ttacgcctct gaagttagca gcctcgctat tcctagcttg    420
actggagcca tggccactgc tgcagcagct gtcgcaaagg ttccctcttt tatgtggcta    480
gatactcttg acaagacccc tctcatggag caaaccttgg ccgacatccg caccgccaac    540
aagaatggcg gtaactatgc cggacagttt gtggtgtatg acttgccgga tcgcgattgc    600
gctgcccttg cctcgaatgg cgaatactct attgccgatg gtggcgtcgc caaatataag    660
aactatatcg acaccattcg tcaaattgtc gtggaatatt ccgatatccg gacccctcctg    720
gttattgagc ctgactctct tgccaacctg gtgaccaacc tcggtactcc aaagtgtgcc    780
aatgctcagt cagcctacct tgagtgcatc aactacgccg tcacacagct gaaccttcca    840
aatgttgcga tgtatttgga cgctggccat gcaggatggc ttggctggcc ggcaaaccaa    900
gacccggccg ctcagctatt tgcaaatgtt tacaagaatg catcgtctcc gagagctctt    960
cgcggattgg caaccaatgt cgccaactac aacgggtgga acattaccag ccccccatcg   1020
tacacgcaag gcaacgctgt ctacaacgag aagctgtaca tccacgctat ggaacctctt   1080
cttgccaatc acggctggtc caacgccttc ttcatcactg atcaaggtcg atcgggaaag   1140
cagcctaccg gacagcaaca gtggggagac tggtgcaatg tgatcggcac cggatttggt   1200
attcgcccat ccgcaaacac tggggactcg ttgctggatt cgtttgtctg ggtcaagcca   1260
ggcggcgagt gtgacggcac cagcgacagc agtcgccac gatttgactc ccactgtgcg   1320
ctcccagatg ccttgcaacc ggcgcctcaa gctggtgctt ggttccaagc ctactttgtg   1380
cagcttctca aaacgcaaa cccatcgttc ctgtaa                              1416
```

<210> SEQ ID NO 16
<211> LENGTH: 471
<212> TYPE: PRT
<213> ORGANISM: Trichoderma reesei

<400> SEQUENCE: 16

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175
```

-continued

```
Arg Thr Ala Asn Lys Asn Gly Gly Asn Tyr Ala Gly Gln Phe Val Val
                180                 185                 190

Tyr Asp Leu Pro Asp Arg Asp Cys Ala Ala Leu Ala Ser Asn Gly Glu
            195                 200                 205

Tyr Ser Ile Ala Asp Gly Gly Val Ala Lys Tyr Lys Asn Tyr Ile Asp
210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 17
<211> LENGTH: 37
<212> TYPE: DNA
<213> ORGANISM: Trichoderma reesei

<400> SEQUENCE: 17
ggaattctag ttcttatatt tggcgacgcc accatct                          37

<210> SEQ ID NO 18
<211> LENGTH: 36
<212> TYPE: DNA
<213> ORGANISM: Trichoderma reesei

<400> SEQUENCE: 18
catgccatgg aaaggttccc tcttttatgt ggctag                           36
```

```
<210> SEQ ID NO 19
<211> LENGTH: 36
<212> TYPE: DNA
<213> ORGANISM: Trichoderma reesei

<400> SEQUENCE: 19
ggaattctga ctgagcattg gcacactttg gagtac                    36

<210> SEQ ID NO 20
<211> LENGTH: 36
<212> TYPE: DNA
<213> ORGANISM: Trichoderma reesei

<400> SEQUENCE: 20
ccttaattaa aaaggttccc tcttttatgt ggctag                    36

<210> SEQ ID NO 21
<211> LENGTH: 20
<212> TYPE: DNA
<213> ORGANISM: Trichoderma reesei

<400> SEQUENCE: 21
aaatcgtggc gcactgctgt                                      20

<210> SEQ ID NO 22
<211> LENGTH: 20
<212> TYPE: DNA
<213> ORGANISM: Trichoderma reesei

<400> SEQUENCE: 22
tgagtgcatc aactacgccg                                      20

<210> SEQ ID NO 23
<211> LENGTH: 20
<212> TYPE: DNA
<213> ORGANISM: Trichoderma reesei

<400> SEQUENCE: 23
gtcaacacga cgaatggcgt                                      20

<210> SEQ ID NO 24
<211> LENGTH: 21
<212> TYPE: DNA
<213> ORGANISM: Trichoderma reesei

<400> SEQUENCE: 24
tgatcggtat gggtcagaag g                                    21

<210> SEQ ID NO 25
<211> LENGTH: 21
<212> TYPE: DNA
<213> ORGANISM: Trichoderma reesei

<400> SEQUENCE: 25
ctggtccaac gccttcttca t                                    21

<210> SEQ ID NO 26
<211> LENGTH: 22
<212> TYPE: DNA
<213> ORGANISM: Trichoderma reesei

<400> SEQUENCE: 26
ggaacgtagt gaggctcgct aa                                   22
```

```
<210> SEQ ID NO 27
<211> LENGTH: 22
<212> TYPE: DNA
<213> ORGANISM: Trichoderma reesei

<400> SEQUENCE: 27
catggctggt cgtgatctta cc                                              22

<210> SEQ ID NO 28
<211> LENGTH: 22
<212> TYPE: DNA
<213> ORGANISM: Trichoderma reesei

<400> SEQUENCE: 28
ccttgatgtc acggacgatt tc                                              22

<210> SEQ ID NO 29
<211> LENGTH: 24
<212> TYPE: DNA
<213> ORGANISM: Trichoderma reesei

<400> SEQUENCE: 29
ccagacatga caatgttgcc gtag                                            24

<210> SEQ ID NO 30
<211> LENGTH: 23
<212> TYPE: DNA
<213> ORGANISM: Trichoderma reesei

<400> SEQUENCE: 30
tttcgctctt cctcacgcca ttg                                             23

<210> SEQ ID NO 31
<211> LENGTH: 25
<212> TYPE: DNA
<213> ORGANISM: Trichoderma reesei

<400> SEQUENCE: 31
ctagtctaga gtcgcaaagg ttccc                                           25

<210> SEQ ID NO 32
<211> LENGTH: 23
<212> TYPE: DNA
<213> ORGANISM: Trichoderma reesei

<400> SEQUENCE: 32
gggggaagct ttgactgagc att                                             23

<210> SEQ ID NO 33
<211> LENGTH: 46
<212> TYPE: DNA
<213> ORGANISM: Aspergillus niger

<400> SEQUENCE: 33
ggggccatgg tcctggtgtg attctcaggc acccgaaatt ctctgc                    46

<210> SEQ ID NO 34
<211> LENGTH: 42
<212> TYPE: DNA
<213> ORGANISM: Aspergillus niger

<400> SEQUENCE: 34
gggggcggcc gcagcagggc tggaaggtgg agtcgtcgca tg                        42
```

```
<210> SEQ ID NO 35
<211> LENGTH: 45
<212> TYPE: DNA
<213> ORGANISM: Aspergillus niger

<400> SEQUENCE: 35
ggggttaatt aatcctggtg tgattctcag gcacccgaaa ttctc            45

<210> SEQ ID NO 36
<211> LENGTH: 42
<212> TYPE: DNA
<213> ORGANISM: Aspergillus niger

<400> SEQUENCE: 36
gggggcggcc gctaccgacc caccgcaaca gcctcgctgt ca               42

<210> SEQ ID NO 37
<211> LENGTH: 42
<212> TYPE: DNA
<213> ORGANISM: Aspergillus niger

<400> SEQUENCE: 37
tttagatctc tcgaggtacc aaatgtgatt ccaagcgcg cg                42

<210> SEQ ID NO 38
<211> LENGTH: 30
<212> TYPE: DNA
<213> ORGANISM: Aspergillus niger

<400> SEQUENCE: 38
tttggatcca agagatcgac gagggtcttg                             30

<210> SEQ ID NO 39
<211> LENGTH: 42
<212> TYPE: DNA
<213> ORGANISM: Aspergillus niger

<400> SEQUENCE: 39
tttagatctc tcgaggtacc aaatgtgatt ccaagcgcg cg                42

<210> SEQ ID NO 40
<211> LENGTH: 30
<212> TYPE: DNA
<213> ORGANISM: Aspergillus niger

<400> SEQUENCE: 40
tttggatcct aggcagtctc atcgacattg                             30

<210> SEQ ID NO 41
<211> LENGTH: 400
<212> TYPE: DNA
<213> ORGANISM: Aspergillus oryzae
<220> FEATURE:
<221> NAME/KEY: misc_feature
<222> LOCATION: (265)..(265)
<223> OTHER INFORMATION: N=A, C, G, OR T

<400> SEQUENCE: 41
ggaaggcaac tatacgaaaa atgctctcaa ttccgggcaa caatgcagca cttcgattgc    60
attagtcaaa accaagggtt tccttcgatc cttcccttgg ttgacggaag cgtgcccgtg   120
gaggagctgg gccctatcgt gacacagctc ggcaccacat gtcttcagat ggctttggtc   180
aactattggg gttcactagg tataaaacct gcgttcgttc ttgggcatag tctcggggag   240
```

```
tttgctgctt tgaataccgc aggantatta tcgacttccg ataccatcta cctttgtggc      300
cgtcgggcta ccctccttac agaatactgc caggttggga cacacgccat gctggctgtc      360
aaggcttcct accccaggt caagcagtta ctgaaagaaa                              400
```

<210> SEQ ID NO 42
<211> LENGTH: 133
<212> TYPE: PRT
<213> ORGANISM: Aspergillus oryzae
<220> FEATURE:
<221> NAME/KEY: MISC_FEATURE
<222> LOCATION: (89)..(89)
<223> OTHER INFORMATION: XAA=ANY AMINO ACID

<400> SEQUENCE: 42

```
Gly Arg Gln Leu Tyr Glu Lys Cys Ser Gln Phe Arg Ala Thr Met Gln
 1               5                  10                  15

His Phe Asp Cys Ile Ser Gln Asn Gln Gly Phe Pro Ser Ile Leu Pro
            20                  25                  30

Leu Val Asp Gly Ser Val Pro Val Glu Glu Leu Gly Pro Ile Val Thr
        35                  40                  45

Gln Leu Gly Thr Thr Cys Leu Gln Met Ala Leu Val Asn Tyr Trp Gly
    50                  55                  60

Ser Leu Gly Ile Lys Pro Ala Phe Val Leu Gly His Ser Leu Gly Glu
65                  70                  75                  80

Phe Ala Ala Leu Asn Thr Ala Gly Xaa Leu Ser Thr Ser Asp Thr Ile
                85                  90                  95

Tyr Leu Cys Gly Arg Arg Ala Thr Leu Leu Thr Glu Tyr Cys Gln Val
            100                 105                 110

Gly Thr His Ala Met Leu Ala Val Lys Ala Ser Tyr Pro Gln Val Lys
        115                 120                 125

Gln Leu Leu Lys Glu
    130
```

<210> SEQ ID NO 43
<211> LENGTH: 37
<212> TYPE: DNA
<213> ORGANISM: Aspergillus oryzae

<400> SEQUENCE: 43

```
gggggcggcc gcagcacttc gattgcatta gtcaaaa                                37
```

<210> SEQ ID NO 44
<211> LENGTH: 30
<212> TYPE: DNA
<213> ORGANISM: Aspergillus oryzae

<400> SEQUENCE: 44

```
gggggctagc agaacgaacg caggttttat                                        30
```

<210> SEQ ID NO 45
<211> LENGTH: 33
<212> TYPE: DNA
<213> ORGANISM: Aspergillus oryzae

<400> SEQUENCE: 45

```
gggggctagc gggtagcccg acggccacaa agg                                    33
```

METHODS FOR ELIMINATING OR REDUCING THE EXPRESSION OF A GENES IN A FILAMENTOUS FUNGAL STRAINS

CROSS-REFERENCE TO RELATED APPLICATION

This application claims the benefit of U.S. Provisional Application No. 60/528,367, filed Dec. 9, 2003, which application is incorporated herein by reference.

BACKGROUND OF THE INVENTION

1. Field of the Invention

The present invention relates to eliminating or reducing expression of a gene in a filamentous fungal strain.

2. Description of the Related Art

Filamentous fungal strains are widely used for the production of biological substances of commercial value. However, filamentous fungal strains with the desirable traits of increased expression and secretion of a biological substance may not necessarily have the most desirable characteristics for successful fermentation. The production of the biological substance may be accompanied by the production of other substances, e.g., enzymes, that degrade the biological substance or co-purify with the biological substance, which can complicate recovery and purification of the biological substance.

One solution to these problems is to inactivate the gene(s) involved in the production of the undesirable substance. Inactivation can be accomplished by deleting or disrupting the gene(s) using methods well known in the art. However, in some cases, inactivation of the gene may be difficult because of poor targeting to homologous regions of the gene. Inactivation can also be accomplished by random mutagenesis, but random mutagenesis is not always specific for the intended target gene and other mutations are often introduced into the host organism. In other situations, the gene and its product may be required for survival of the filamentous fungal strain. Where multiple genes are to be inactivated by deletion or disruption, the task can be very cumbersome and time-consuming. When highly homologous members of gene families exist, deletion or disruption of all members can be extremely tedious and difficult.

In recent years various forms of epigenetic gene regulation have been described (Selker, 1997, *Trends Genet.* 13: 296-301; Matzke and Matzke, 1998, *Cell. Mol. Life. Sci.* 54: 94-103). These processes influence gene expression by modulating the levels of messenger RNA (Hammond and Baulcombe, 1996, *Plant Mol. Biol.* 32: 79-88; Xi-song Ke et al., 2003, *Current Opinion in Chemical Biology* 7: 516-523) via micro RNAs (Morel et al., 2000, *Curr. Biol.* 10: 1591-4; Bailis and Forsburg, 2002, *Genome Biol.* 3, Reviews 1035; Grewal and Moazed, 2003, *Science* 301: 798-802).

Based on genetic studies of *Drosophila* and *Caenorhabditis elegans*, RNA interference (RNAi), also known as post-transcriptional gene silencing (in plants), is understood to involve silencing the expression of a gene by assembly of a protein-RNA effector nuclease complex that targets homologous RNAs for degradation (Hannon, 2002, *Nature* 418: 244-251). The processing of double-stranded RNA (dsRNA) into small interfering RNAs is accomplished by a family of enzymes known as Dicer (Bernstein et al., 2001, *Nature* 409: 363). Dicer, a member of the RNase III family of endonucleases that specifically cleaves dsRNA, is responsible for digestion of dsRNA into siRNAs ranging from 20-25 nucleotides (Elbashir et al., 2001, *Nature* 411: 494). These siRNAs denature with the anti-sense strand and then associate with the RNA Induced Silencing Complex (RISC) (Elbashir et al., 2001, *Genes and Dev.* 15: 188; NyKanen et al., 2001, *Cell* 197: 300; Hammond et al., 2001, *Science* 293: 1146.). Although not well understood, RISC targets the mRNA from which the anti-sense fragment was derived followed by endo and exonuclease digestion of the mRNA effectively silencing expression of that gene. RNAi has been demonstrated in plants, nematodes, insects, and mammals (Matzke and Matzke, 1998, supra; Kennerdell et al., 2000, *Nat. Biotechnol.* 18: 896-8; Bosher et al., 1999, *Genetics* 153: 1245-56; Voorhoeve and Agami, 2003, *Trends Biotechnol.* 21: 2-4; and McCaffrey et al., 2003, *Nat Biotechnol.* 21: 639-44).

WO 98/53083 discloses constructs and methods for enhancing the inhibition of a target gene within a plant by inserting a silencing vector comprising an inverted repeat sequence of all or part of the target gene into the genome of a plant.

WO 01/49844 describes an inverted repeat gene construct encoding an inverted repeat gene, comprising a promoter element operably linked in a 5' to 3' direction to a first coding sequence and a second sequence in an antisense orientation for disrupting gene expression in targeted organisms, such as *Caenorhabditis elegans*, yeast, *Dictostelium*, *Drosophila*, mice, plants, insects, human cells, and nematodes.

WO 03/050288 discloses methods of silencing a target gene in a plant by providing a recombinant DNA construct comprising a promoter operably linked to a chimeric nucleotide sequence encoding all or part of the target gene and a transgene, transforming the plant with the DNA construct such that the expression cassette is inserted into the genome, and initiating post-transcriptional gene silencing of the transgene in the plant, whereby initiation of post-transcriptional gene silencing of the transgene causes silencing of the target gene.

It would be an advantage in the art to have alternative methods for eliminating or reducing the expression of one or more genes for strain development and improvement, functional genomics, and pathway engineering of filamentous fungal strains.

It is an object of the present invention to provide alternative methods for eliminating or reducing the expression of one or more genes in a filamentous fungal strain.

SUMMARY OF THE INVENTION

The present invention relates to methods for reducing or eliminating the expression of a target gene encoding a biological substance in a filamentous fungal strain, comprising:
(a) inserting into the genome of the filamentous fungal strain a double-stranded transcribable nucleic acid construct comprising a first nucleotide sequence comprising a promoter operably linked to a first homologous transcribable region of the target gene encoding the biological substance and a second nucleotide sequence comprising a second homologous transcribable region of the target gene, wherein the first and second homologous regions are complementary to each other and the second homologous region is in reverse orientation relative to the first homologous region; and
(b) inducing production of an interfering RNA encoded by the double-stranded transcribable nucleic acid construct by cultivating the filamentous fungal strain under conditions conducive for production of the interfering RNA, wherein the interfering RNA interacts with RNA transcripts of the target gene to reduce or eliminate expression of the target gene encoding the biological substance.

The present invention also relates to filamentous fungal strains comprising a nucleic acid construct comprising a double-stranded transcribable nucleic acid construct comprising a first nucleotide sequence comprising a promoter operably linked to a first homologous region of a target gene encoding a biological substance and a second nucleotide sequence comprising a second homologous region or a portion thereof of the target gene, wherein the first and second homologous regions are complementary to each other and the second homologous region is in reverse orientation relative to the first homologous region, wherein interfering RNA encoded by the double-stranded transcribable nucleic acid construct interacts with RNA transcripts of the target gene to reduce or eliminate expression of the target gene encoding the biological substance.

The present invention further relates to methods for producing a biological substance, comprising:

(a) cultivating a filamentous fungal strain under conditions conducive for production of the biological substance of interest, wherein the filamentous fungal strain comprises a double-stranded transcribable nucleic acid construct comprising a first nucleotide sequence comprising a promoter operably linked to a first homologous transcribable region of a target gene encoding an undesirable biological substance and a second nucleotide sequence comprising a second homologous transcribable region of the target gene, wherein the first and second homologous regions are complementary to each other and the second homologous region is in reverse orientation relative to the first homologous region, wherein interfering RNA encoded by the double-stranded transcribable nucleic acid construct interacts with RNA transcripts of the target gene to reduce or eliminate expression of the target gene encoding the undesirable biological substance; and wherein the filamentous fungal strain comprises a third nucleotide sequence encoding the biological substance of interest; and (b) recovering the biological substance from the cultivation medium.

DETAILED DESCRIPTION OF THE INVENTION

Figure 1:
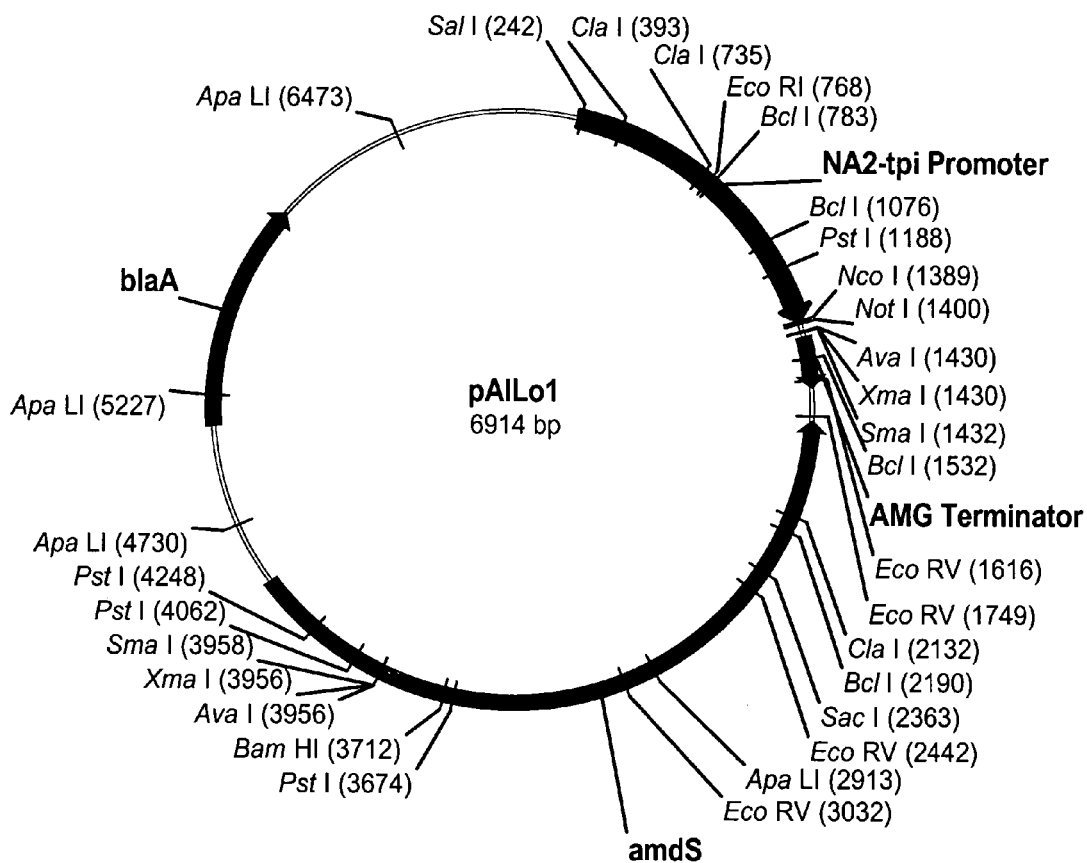
FIG. 1 shows a restriction map of pAILo1.

The present invention relates to methods for reducing or eliminating the expression of a target gene encoding a biological substance in a filamentous fungal strain, comprising: (a) inserting into the genome of the filamentous fungal strain a double-stranded transcribable nucleic acid construct comprising a first nucleotide sequence comprising a promoter operably linked to a first homologous transcribable region of the target gene and a second nucleotide sequence comprising a second homologous transcribable region of the target gene encoding the biological substance, wherein the first and second homologous regions are complementary to each other and the second homologous region is in reverse orientation relative to the first homologous region; and (b) inducing production of an interfering RNA encoded by the double-stranded transcribable nucleic acid construct by cultivating the filamentous fungal strain under conditions conducive for production of the interfering RNA, wherein the interfering RNA interacts with RNA transcripts of the target gene to reduce or eliminate expression of the target gene encoding the biological substance.

The methods of the present invention provide new opportunities for strain development and improvement, functional genomics, and pathway engineering in filamentous fungal strains. For example, the present methods can be used as a tool for filamentous fungal host strain development by means of gene manipulation and pathway engineering or as a replacement for gene knockouts, a time consuming approach with variable rates of success. A gene may be resistant to inactivation by standard methods known in the art such as gene knockout. The methods of the present invention provide a solution to reducing or eliminating the expression of such a gene. The methods are also particularly useful and efficient for reducing or eliminating a highly expressed gene in a particular filamentous fungal strain, which can be very important, for example, in developing the organism as a production host. This ability demonstrates the strength of the methods of the present invention. The methods are also useful for reducing or eliminating the expression of a multiple of genes that are highly homologous to each other, especially genes of the same family or homologous genes in a biosynthetic or metabolic pathway. The methods are further useful because they can be manipulated to cause a variable reduction in the expression of a biological substance. This variability is especially important where a complete knock-out of a gene encoding a biological substance would be lethal to a particular filamentous fungal strain, such as in a secondary pathway that feeds into a biosynthetic pathway of interest.

In the methods of the present invention, the first nucleotide sequence comprises a promoter operably linked to a first homologous transcribable region of the target gene. The second nucleotide sequence comprises a second homologous transcribable region of the target gene, where the first and second homologous regions are complementary to each other and the second homologous region is in reverse orientation relative to the first homologous region. In a preferred aspect, the first and second nucleotide sequences are separated by a third nucleotide sequence to stabilize the first and second nucleotide sequences in a filamentous fungal strain against undesirable recombination during construction, such as in *E. coli*. The nucleotide sequences of the double-stranded transcribable nucleic acid construct may be of genomic, cDNA, RNA, semisynthetic, synthetic origin, or any combinations thereof.

Promoter

The term "promoter" is defined herein as a DNA sequence that binds RNA polymerase and directs the polymerase to the correct downstream transcriptional start site of a nucleic acid sequence encoding a biological substance to initiate transcription. RNA polymerase effectively catalyzes the assembly of messenger RNA complementary to the appropriate DNA strand of a coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors. The promoter sequence may be native or foreign (heterologous) to the first homologous transcribable region and native or foreign to the filamentous fungal strain. In the methods of the present invention, the promoter can be a native promoter, heterologous promoter, mutant promoter, hybrid promoter, or tandem promoter.

The term "mutant promoter" is defined herein as a promoter having a nucleotide sequence comprising a substitution, deletion, and/or insertion of one or more nucleotides of a parent promoter, wherein the mutant promoter has more or less promoter activity than the corresponding parent promoter. The term "mutant promoter" also encompasses natural mutants and in vitro generated mutants obtained using methods well known in the art such as classical mutagenesis, site-directed mutagenesis, and DNA shuffling.

The term "hybrid promoter" is defined herein as parts of two more promoters that are fused together to generate a sequence that is a fusion of the two or more promoters, which when operably linked to a coding sequence mediates the transcription of the coding sequence into mRNA.

The term "tandem promoter" is defined herein as two or more promoter sequences each of which is operably linked to a coding sequence and mediates the transcription of the coding sequence into mRNA.

The term "operably linked" is defined herein as a configuration in which a promoter sequence is appropriately placed at a position relative to the homologous regions of the target gene such that the promoter sequence directs the transcription of the two regions.

Examples of promoters useful in the methods of the present invention include the promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Coprinus cinereus* beta-tubulin, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

Homologous Transcribable Region

The term "homologous transcribable region" is defined herein as a nucleotide sequence which is homologous to the open reading frame of a target gene or a portion thereof; that is transcribed into an RNA, e.g., ncRNA (non-coding RNA), tRNA (transfer RNA), rRNA (ribosomal RNA), mRNA (micro RNA), or mRNA (messenger RNA), which may or may not be translated into a biological substance, e.g., polypeptide, when placed under the control of the appropriate regulatory sequences. The boundaries of the transcribable region are generally determined by the transcription start site located just upstream of the open reading frame at the 5' end of the mRNA and a transcription terminator sequence located just downstream of the open reading frame at the 3' end of the mRNA. A homologous transcribable region can include, but is not limited to, genomic DNA, cDNA, semisynthetic, synthetic, and recombinant nucleic acid sequences.

In the methods of the present invention, the first region homologous to the target gene may be identical to the corresponding region of the target gene or may be a homologue thereof.

The degree of identity between the homologue and the corresponding region of the target gene required to achieve inactivation or reduction of the expression of the target gene will likely depend on the target gene. The smaller the homologue's nucleotide sequence is relative to the entire target gene, the degree of identity between the sequences should preferably be very high or identical. The larger the homologue's nucleotide sequence is relative to the entire target gene, the degree of identity between the sequences can likely be lower.

In the methods of the present invention, the degree of identity of the homologue's nucleotide sequence to the corresponding region of the target gene is at least 65%, preferably at least 70%, more preferably at least 75%, more preferably at least 80%, more preferably at least 85%, more preferably at least 90%, even more preferably at least 95%, and most preferably at least 97%. For purposes of the present invention, the degree of identity between two nucleic acid sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Alternatively, the ability of the homologue and the corresponding region of the target gene to hybridize to each other under various stringency conditions can also provide an indication of the degree of relatedness required for inactivation or reduction of expression of a target gene. However, it should be recognized that the lower the stringency conditions required, e.g., low stringency, to achieve hybridization between the homologue and the corresponding region of the target gene, inactivation or reduction of the expression of the target gene will likely be less efficient. In a preferred aspect, the homologue and the corresponding region of the target gene hybridize under low stringency conditions. In a more preferred aspect, the homologue and the corresponding region of the target gene hybridize under medium stringency conditions. In an even more preferred aspect, the homologue and the corresponding region of the target gene hybridize under medium-high stringency conditions. In a most preferred aspect, the homologue and the corresponding region of the target gene hybridize under high stringency conditions. In an even most preferred aspect, the homologue and the corresponding region of the target gene hybridize under very high stringency conditions.

For probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The first homologous region preferably consists of at least 19 nucleotides, more preferably at least 40 nucleotides, more preferably at least 60 nucleotides, more preferably at least 80 nucleotides, even more preferably at least 100 nucleotides, and most preferably at least 200 nucleotides. The first homologous region can also consist of the entire open reading frame of the gene or a homologue thereof.

Inverted Repeat

The double-stranded transcribable nucleic acid construct also comprises a second homologous transcribable region of the target gene, where the first and second homologous regions are complementary to each other and the second homologous region is in reverse orientation relative to the first homologous region, i.e., an inverted repeat of the first homologous region.

In a preferred aspect, the second homologous region is 100% identical to the first homologous region, but in reverse orientation relative to the first homologous region. In another preferred aspect, the second homologous region is a portion of the first homologous region, wherein the portion is 100% identical to the corresponding portion of the first homologous region. In another preferred aspect, the second homologous region is a homologue of the corresponding portion of the first homologous region. In another preferred aspect, the second homologous region is a homologue portion of the corresponding portion of the first homologous region.

The homologue or homologue portion is at least 65%, preferably at least 70%, more preferably at least 75%, more preferably at least 80%, more preferably at least 85%, more preferably at least 90%, even more preferably at least 95%, and most preferably at least 97% identical to the corresponding sequence of the first nucleotide sequence. Percent identity is determined according to the Wilbur-Lipman method described herein.

The second homologous region which identifies the gene targeted for reducing or eliminating expression may be any homologous transcribable part of the target gene, such as the 5'-untranslated region, the biological substance coding sequence, or the 3'-untranslated region of the target gene.

In a preferred aspect, the second homologous region corresponds to the biological substance coding sequence of the target gene, or a portion thereof.

In another preferred aspect, the second homologous region corresponds to the 5'-untranslated region of the target gene, or a portion thereof.

In another preferred aspect, the second homologous region corresponds to the 3'-untranslated region of the target gene, or a portion thereof.

The second homologous region preferably consists of at least 19 nucleotides, more preferably at least 40 nucleotides, more preferably at least 60 nucleotides, more preferably at least 80 nucleotides, even more preferably at least 100 nucleotides, and most preferably at least 200 nucleotides. The second homologous region can also consist of the entire open reading frame of the gene or a homologue thereof.

Spacer Between First and Second Nucleotide Sequences

The first and second nucleotide sequences comprising the homologous regions of the target gene may or may not be separated by a polynucleotide linker or spacer, which is a nucleotide sequence which has little or no homology to the first and second nucleotide sequences in the double-stranded transcribable nucleic acid construct.

In a preferred aspect, the first and second nucleotide sequences are separated by a polynucleotide linker. The spacer preferably consists of at least 5 nucleotides, more preferably at least 10 nucleotides, more preferably at least 20 nucleotides, more preferably at least 30 nucleotides, more preferably at least 40 nucleotides, even more preferably at least 500 nucleotides, and most preferably at least 100 nucleotides.

The spacer or linker can be any nucleotide sequence without homology to the first or second nucleotide sequence and preferably having little or no homology to sequences in the genome of the filamentous fungal strain to minimize undesirable targeting/recombination.

Target Gene

The target gene may be any gene encoding a biological substance. The biological substance may be an RNA (e.g., ncRNA, rRNA, tRNA, mRNA, or mRNA). The biological substance may also be any biopolymer or metabolite. The biological substance may be encoded by a single gene or a series of genes composing a biosynthetic or metabolic pathway or may be the direct result of the product of a single gene or products of a series of genes. The biological substance may be native to the filamentous fungal strain or foreign or heterologous to the strain. The term "heterologous biological substance" is defined herein as a biological substance which is not native to the cell; or a native biological substance in which structural modifications have been made to alter the native biological substance.

In the methods of the present invention, the biopolymer may be any biopolymer. The term "biopolymer" is defined herein as a chain (or polymer) of identical, similar, or dissimilar subunits (monomers). The biopolymer may be, but is not limited to, a nucleic acid, polyamine, polyol, polypeptide (or polyamide), or polysaccharide.

In a preferred aspect, the biopolymer is a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the filamentous fungal cell. Polypeptides further include naturally occurring allelic and engineered variations of the above-mentioned polypeptides and hybrid polypeptides.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is a collagen or gelatin, or a variant or hybrid thereof.

In another preferred aspect, the biopolymer is a polysaccharide. The polysaccharide may be any polysaccharide, including, but not limited to, a mucopolysaccharide (e.g., heparin and hyaluronic acid) and nitrogen-containing polysaccharide (e.g., chitin). In a more preferred aspect, the polysaccharide is hyaluronic acid.

In the methods of the present invention, the metabolite may be any metabolite. The metabolite may be encoded by one or more genes, such as a biosynthetic or metabolic pathway. The term "metabolite" encompasses both primary and secondary metabolites. Primary metabolites are products of primary or general metabolism of a cell, which are concerned with energy metabolism, growth, and structure. Secondary metabolites are products of secondary metabolism (see, for example, R. B. Herbert, *The Biosynthesis of Secondary Metabolites*, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. In a preferred aspect, the secondary metabolite is an antibiotic, antifeedant, attractant, bacteriocide, fungicide, hormone, insecticide, or rodenticide.

The biological substance may also be the product of a selectable marker. A selectable marker is a gene the product of which provides for biocide or viral resistance, resistance to heavy metals, prototrophy to auxotrophs, and the like. Selectable markers include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

It may be necessary in the practice of the present invention to isolate the target gene. The techniques used to isolate or clone a gene are known in the art and include isolation from genomic DNA, preparation from cDNA, or a combination thereof. The cloning of the gene from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the gene encoding a biological substance, insertion of the fragment into a vector molecule, and incorporation of the recombinant vector into a filamentous fungal cell where multiple copies or clones of the nucleic acid sequence will be replicated. The nucleic acid sequence may be of genomic, cDNA, RNA, semisynthetic, synthetic origin, or any combinations thereof.

In a preferred aspect, expression of the target gene is reduced by at least 20%, preferably at least 30%, more preferably at least 40%, more preferably at least 50%, more preferably at least 60%, more preferably at least 70%, even more preferably at least 80%, and most preferably at least 90%. In another preferred aspect, expression of the target gene is eliminated.

Where it is desired to use an inverted repeat sequence within the 5' untranslated region, the coding sequence, or the 3' untranslated region, gene silencing vectors constructed with inverted repeats within any one of these regions may additionally enable the silencing of genes that are homologous to the coding sequence present in the silencing vector. When it is, therefore, desired to silence homologues of a gene within an organism, the construction of a silencing vector containing an inverted repeat within the 5' untranslated region, the coding sequence, or the 3' untranslated region may allow the elimination or reduction of expression of one or more genes exhibiting sequence homology to the coding sequence within the construct. The term "homology" or "homologous" usually denotes those sequences which are of some common ancestral structure and exhibit a high degree of sequence similarity of the active regions.

In a preferred aspect, the interfering RNA interacts with RNA transcripts of one or more homologues of the target gene to reduce or eliminate expression of the one or more homologues of the target gene.

In a more preferred aspect, expression of one or more homologues of the target gene is reduced by at least 20%, preferably at least 30%, more preferably at least 40%, more preferably at least 50%, more preferably at least 60%, more preferably at least 70%, even more preferably at least 80%, and most preferably at least 90%. In another preferred aspect, expression of one or more homologues of the target gene is eliminated.

Filamentous Fungal Strains

The present invention also relates to filamentous fungal strains comprising a double-stranded transcribable nucleic acid construct comprising a first nucleotide sequence comprising a promoter operably linked to a first homologous transcribable region of the target gene and a second nucleotide sequence comprising a second homologous transcribable region of the target gene, wherein the first and second homologous regions are complementary to each other and the second homologous region is in reverse orientation relative to the first homologous region, wherein the first and second nucleotide sequences form a transcribable duplex polynucleotide comprising a region homologous to a target gene which silences the expression of the target gene in a filamentous fungal strain.

The filamentous fungal strain may be any filamentous fungal strain useful in the methods of the present invention. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a preferred aspect, the filamentous fungal strain is an *Acremonium*, *Aspergillus*, *Aureobasidium*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* strain.

In a more preferred aspect, the filamentous fungal strain is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another more preferred aspect, the filamentous fungal strain is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another more preferred aspect, the filamentous fungal strain is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Coprinus cinereus*, *Coriolus hirsutus*, *Humicola insolens*, *Humicola lanuginosa*, *Mucor miehei*, *Mycellophthora thermophila*, *Neurospora crassa*, *Penicllium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

In a most preferred aspect, the *Aspergillus oryzae* strain is *Aspergillus oryzae* strain deposit no. IFO 4177. In another most preferred aspect, the *Fusarium venenatum* strain is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another preferred aspect, the *Fusarium venenatum* strain is a morphological mutant of *Fusarium venenatum* A3/5 or *Fusarium venenatum* ATCC 20334, as disclosed in WO 97/26330. In another preferred aspect, the *Trichoderma reesei* strain is *Trichoderma reesei* ATCC 56765.

Filamentous fungal strains may be transformed by a process involving protoplast formation, transformation of the protoplasts, and regeneration of the cell wall in a manner known per se. Suitable procedures for transformation of *Aspergillus* and *Trichoderma* strains are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Reduction or elimination of expression of a target gene encoding a biological substance may be detected using methods known in the art that are specific for the targeted biological substance. These detection methods may include use of specific antibodies, high performance liquid chromatography, capillary electrophoresis, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

Methods of Production

The present invention also relates to methods for producing a biological substance of interest, comprising: (a) cultivating a filamentous fungal strain under conditions conducive for production of the biological substance of interest, wherein the filamentous fungal strain comprises a double-stranded transcribable nucleic acid construct comprising a first nucleotide sequence comprising a promoter operably linked to a first homologous transcribable region of a target gene encoding an undesirable biological substance and a second nucleotide sequence comprising a second homologous transcribable region of the target gene, wherein the first and second homologous regions are complementary to each other and the second homologous region is in reverse orientation relative to the first homologous region, wherein interfering RNA encoded by the double-stranded transcribable nucleic acid construct interacts with RNA transcripts of the target gene to reduce or eliminate expression of the target gene encoding the undesirable biological substance; and wherein the filamentous fungal strain comprises a third nucleotide sequence encoding the biological substance of interest; and (b) recovering the biological substance of interest from the cultivation medium.

The biological substance of interest may any biological substance as described herein. It may be native or foreign to the filamentous fungal strain. The reduction or elimination of expression of the target gene encoding the undesirable biological substance can lead to increased expression of another biological substance of interest. The undesirable biological substance could directly affect production or expression of the biological substance of interest. For example, the undesirable biological substance may be a protease that attacks the biological substance of interest thereby lowering the amount of the biological substance of interest produced. By reducing or eliminating expression of the protease, more of the biological substance of interest will be expressed and produced. Or, the undesirable biological substance may share a cellular process or processes, e.g., transcription factor or secretory pathway, with the biological substance of interest thereby lowering the amount of the biological substance of interest produced. By reducing or eliminating expression of the undesirable biological substance, more of the cellular process or processes will be available to the biological substance of interest, e.g., expression-limiting transcription elements, thereby increasing the amount of the biological substance of interest expressed and produced. Moreover, the undesirable biological substance may be a toxin that contaminates the biological substance of interest preventing the use of the biological substance of interest in a particular application, e.g., an enzyme in a food process.

In the production methods of the present invention, the filamentous fungal strains are cultivated in a nutrient medium suitable for production of the biological substance of interest using methods known in the art. For example, the strain may be cultivated by shake flask cultivation, and small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the biological substance is secreted into the nutrient medium, it can be recovered directly from the medium. If the biological substance is not secreted, it can be recovered from cell lysates.

The biological substance of interest may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance of interest may be isolated using methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

Nucleotide Sequences

The nucleotide sequence encoding the biological substance of interest may be obtained from any prokaryotic, eukaryotic, or other source. For purposes of the present invention, the term "obtained from" as used herein in connection with a given source shall mean that the biological substance is produced by the source or by a cell in which a gene from the source has been inserted.

The techniques used to isolate or clone a nucleotide sequence encoding a biological substance of interest are known in the art and include isolation from genomic DNA, preparation from cDNA, or a combination thereof. The cloning of the nucleotide sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleotide sequence encoding the biological substance, insertion of the fragment into a vector molecule, and incorporation of the recombinant vector into the mutant filamentous fungal cell where multiple copies or clones of the nucleic acid sequence will be replicated. The nucleic acid sequence may be of genomic, cDNA, RNA, semisynthetic, synthetic origin, or any combinations thereof.

Nucleic Acid Constructs

The nucleotide sequence encoding the biological substance of interest may be contained in a nucleic acid construct in the filamentous fungal strain. A nucleic acid construct comprises a nucleotide sequence encoding the biological substance of interest operably linked to at least one promoter and one or more control sequences which direct the expression of the nucleotide sequence in a filamentous fungal strain under conditions compatible with the control sequences. Expression will be understood to include any step involved in the production of the biological substance of interest including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleotide sequence encoding the biological substance of interest may be further manipulated in a variety of ways to provide for expression of the biological substance. Manipulation of the nucleotide sequence prior to its insertion into a vector may be desirable or necessary depending on the expression vector. The techniques for modifying nucleotide sequences utilizing recombinant DNA methods are well known in the art.

The nucleotide sequence may comprise one or more native control sequences or one or more of the native control sequences may be replaced with one or more control sequences foreign to the nucleotide sequence for improving expression of the coding sequence in a host cell.

The term "control sequences" is defined herein to include all components which are necessary or advantageous for expression of a biological substance of interest. Each control sequence may be native or foreign to the nucleotide sequence encoding the biological substance. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a biological substance of interest.

The control sequence may be a suitable transcription terminator sequence, a sequence recognized by a host cell to terminate transcription. The terminator sequence is operably linked to the 3' terminus of the nucleic acid sequence encoding the biological substance. Any terminator which is functional in the filamentous fungal strain of choice may be used in the present invention.

Preferred terminators for filamentous fungal strain are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA which is important for translation by the filamentous fungal strain. The leader sequence is operably linked to the 5' terminus of the nucleic acid sequence encoding the biological substance. Any leader sequence that is functional in the filamentous fungal strain of choice may be used in the present invention.

Preferred leaders for filamentous fungal strains are obtained from the genes for *Aspergillus oryzae* TAKA amylase, *Aspergillus nidulans* triose phosphate isomerase, *Fusarium venenatum* trypsin, and *Fusarium venenatum* glucoamylase.

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the filamentous fungal strain of choice may be used in the present invention.

Preferred polyadenylation sequences for filamentous fungal strains are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a fungal host cell of choice may be used in the present invention.

Effective signal peptide coding regions for filamentous fungal strains are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the biological substance relative to the growth of the filamentous fungal strain. Examples of regulatory systems are those which cause the expression of the gene to be turned on or off in response to a chemical or physical stimulus, including the presence of a regulatory compound. In filamentous fungi, the TAKA alpha-amylase promoter, *Aspergillus niger* glucoamylase promoter, *Aspergillus oryzae* glucoamylase promoter, and *Fusarium venenatum* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the biological substance of interest would be operably linked with the regulatory sequence.

Expression Vectors

The nucleotide sequence encoding the biological substance of interest may be contained in a recombinant expression vector comprising a promoter, the nucleotide sequence encoding the biological substance, and transcriptional and translational stop signals. The various nucleic acid and control sequences described above may be joined together to produce a recombinant expression vector which may include one or more convenient restriction sites to allow for insertion or substitution of the promoter and/or nucleic acid sequence encoding the biological substance at such sites. Alternatively, the nucleotide sequence may be expressed by inserting the nucleotide sequence or a nucleic acid construct comprising a promoter and/or sequence into an appropriate vector for expression. In creating the expression vector, the coding sequence is located in the vector so that the coding sequence is operably linked with a promoter and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors preferably contain one or more selectable markers which permit easy selection of transformed cells. A selectable marker is a gene the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*. Preferred for use in a *Fusarium* cell is the bar, amdS, pyrG, or hygB gene.

The vectors preferably contain an element(s) that permits stable integration of the vector into the host cell's genome or autonomous replication of the vector in the cell independent of the genome.

For integration into the host cell genome of a filamentous fungal strain, the vector may rely on the nucleotide sequence encoding the biological substance or any other element of the vector for stable integration of the vector into the genome by homologous or nonhomologous recombination. Alternatively, the vector may contain additional nucleic acids for directing integration by homologous recombination into the genome of the host cell. The additional nucleic acid sequences enable the vector to be integrated into the host's genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of a plasmid replicator useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence encoding a biological substance of interest may be inserted into the filamentous fungal strain to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

The present invention is further described by the following examples which should not be construed as limiting the scope of the invention.

EXAMPLES

Media and Buffer Solutions

COVE selection plates were composed per liter of 342.3 g of sucrose, 20 ml of COVE salt solution, 10 mM acetamide, 15 mM $CsCl_2$, and 25 g or 30 g of Noble agar.

COVE2 plates were composed per liter of 30 g of sucrose, 20 ml of COVE salt solution, 10 mM acetamide, and 25 g or 30 g of Noble agar.

COVE salt solution was composed per liter of 26 g of KCl, 26 g of $MgSO_4.7H_2O$, 76 g of $KH_2PO_4$, and 50 ml of COVE trace metals.

COVE trace metals was composed per liter of 0.04 g of $NaB_4O_7.10H_2O$, 0.4 g of $CuSO_4.5H_2O$, 1.2 g of $FeSO_4.7H_2O$, 0.7 g or 1 g of $MnSO_4.H_2O$, 0.8 g of $Na_2MoO_2.2H_2O$, and 10 g of $ZnSO_4.7H_2O$.

COVE top agarose was composed per liter of 342.3 g of sucrose, 20 ml of COVE salt solution, 10 mM acetamide, and 10 g of low melt agarose.

Cellulase-inducing medium was composed per liter of 20 g of Arbocel-natural cellulose fibers (J. Rettenmaier USA LP), 10 g of corn steep solids (Sigma Chemical Co., St. Louis, Mo.), 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma reesei* trace metals solution, and 2 drops of pluronic acid. The pH was adjusted to 6.0 with 10 N NaOH before autoclaving.

*Trichoderma reesei* trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

YP medium was composed per liter of 10 g of yeast extract and 20 g of Bacto peptone.

YPG medium was composed per liter of 4 g of yeast extract, 1 g of $K_2HPO_4$, 0.5 g of $MgSO_4$, and 15.0 g of glucose (pH 6.0).

PEG Buffer was composed per liter of 500 g of PEG 4000, 10 mM CaCl$_2$, and 10 mM Tris-HCl pH 7.5, filter sterilized.

STC was composed per liter of 0.8 M or 1 M sorbitol, 10 mM or 25 mM CaCl$_2$, and 10 mM or 25 mM Tris-HCl, pH 7.5 or pH 8, filter sterilized.

STPC was composed of 40% PEG4000 in STC.

M400 medium was composed per liter of 50 g of Maltodextrin, 2 g of MgSO$_4$.7H$_2$O, 2 g of KH$_2$PO$_4$, 4 g of citric acid, 8 g of yeast extract, 2 g of urea, 0.5 g of CaCl$_2$, and 0.5 ml of AMG trace metals solution.

AMG trace metals solution was composed per liter of 6.8 g of ZnCl$_2$.7H$_2$O, 2.5 g of CuSO$_4$.5H$_2$O, 0.24 g of NiCl$_2$.6H$_2$O, 13.9 g of FeSO$_4$.7H$_2$O, 13.5 g of MnSO$_4$.H$_2$O, and 3 g of citric acid.

Minimal medium plates were composed per liter of 6 g of NaNO$_3$, 0.52 g of KCl, 1.52 g of KH$_2$PO$_4$, 1 ml of COVE trace metals, 1 g of glucose, 500 mg of MgSO$_4$.7H$_2$O, 342.3 g of sucrose, and 20 g of Noble agar per liter (pH 6.5).

MLC was composed per liter of 40 g of glucose, 50 g of soybean powder, and 4 g of citric acid, pH 5.0.

MU-1 was composed per liter of 260 g of maltdextrin (MD-11), 5 g of KH$_2$PO$_4$, 3 g of MgSO$_4$.7H$_2$O, 6 g of K$_2$SO$_4$, 5 ml of AMG trace metals solution, and 2 g of urea, pH 4.5.

CM-1 agar plates at pH 6.5 were composed per liter of 0.25 g of NaCl, 0.5 g of MgSO$_4$.7H$_2$O, 1.9 g of K$_2$HPO$_4$, 3.6 g of KH$_2$PO$_4$, 0.1 ml of trace metals solution, 30 g of Bacto agar (Difco), pH 6.5, 11 ml of 10% urea, and 67 ml of 30% maltose.

The trace metals solution (1000×) was composed per liter of 22 g of ZnSO$_4$.7H$_2$O, 11 g of H$_3$BO$_3$, 5 g of MnCl$_2$.4H$_2$O, 5 g of FeSO$_4$.7H$_2$O, 1.6 g of CoCl$_2$.5H$_2$O, 1.6 g of (NH$_4$)$_6$Mo$_7$O$_{24}$, and 50 g of Na$_4$EDTA.

PDA plates were composed per liter of 39 g of Potato Dextrose Agar (Difco).

Example 1

Construction of pAILo1 Expression Vector

Expression vector pAILo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050):
5'-GTGCCCCATGATACGCCTCCGG-3'          (SEQ ID NO: 1)

AMDS2NcoMut (2721):
5'-GAGTCGTATTTCCAAGGCTCCTGACC-3'      (SEQ ID NO: 2)

AMDS1NcoMut (3396):
5'-GGAGGCCATGAAGTGGACCAACGG-3'        (SEQ ID NO: 3)
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to Mutagenize the AMG Terminator Sequence:

```
                                        (SEQ ID NO: 4)
Upper Primer to mutagenize
the AMG terminator sequence:
5'-CACCGTGAAAGCCATGCTCTTTCCTTCGTGTAGAAGACCAGACAG-
                                                  3'
```

Lower Primer to Mutagenize the AMG Terminator Sequence:

```
                                        (SEQ ID NO: 5)
Lower Primer to mutagenize
the AMG terminator sequence:
5'-CTGGTCTTCTACACGAAGGAAAGAGCATGGCTTTCACGGTGTCTG-
                                                  3'
```

The last step in the modification of pBANe6 was the addition of a new Nco I restriction site at the beginning of the polylinker using a QuickChange Mutagenesis Kit and the following primers (underlined nucleotides represent the changed bases) to yield pAILo1 (FIG. 1).

Upper Primer to Mutagenize the NA2-tpi Promoter:

```
                                        (SEQ ID NO: 6)
Upper Primer to mutagenize
the NA2-tpi promoter:
5'-CTATATACACAACTGGATTTACCATGGGCCCGCGGCCGCAGATC-3'
```

Lower Primer to Mutagenize the NA2-tpi Promoter:

```
                                        (SEQ ID NO: 7)
Lower Primer to mutagenize
the NA2-tpi promoter:
5'-GATCTGCGGCCGCGGGCCCATGGTAAATCCAGTTGTGTATATAG-3'
```

Example 2

Construction of pMJ04 Expression Vector

Expression vector pMJ04 was constructed by first PCR amplifying the *Trichoderma reesei* Cel7A cellobiohydrolase 1 gene (cbh1) terminator from *Trichoderma reesei* RutC30 genomic DNA using primers 993429 (antisense) and 993428 (sense) shown below. The antisense primer was engineered to have a Pac I site at the 5'-end and a Spe I site at the 5'-end of the sense primer. *Trichoderma reesei* RutC30 (ATCC 56765; Montenecourt and Eveleigh, 1979, *Adv. Chem. Ser.* 181: 289-301) was derived from *Trichoderma reesei* Qm6A (ATCC 13631; Mandels and Reese, 1957, *J. Bacteriol.* 73: 269-278).

Primer 993429 (Antisense):

```
Primer 993429 (antisense):
5'-AACGTTAATTAAGGAATCGTTTTGTGTTT-3'    (SEQ ID NO: 8)
```

Primer 993428 (Sense):

```
Primer 993428 (sense):
5'-AGTACTAGTAGCTCCGTGGCGAAAGCCTG-3'    (SEQ ID NO: 9)
```

The amplification reactions (50 μl) were composed of 1× ThermoPol Reaction Buffer (New England Biolabs, Beverly, Mass.), 0.3 mM dNTPs, 100 ng of *Trichoderma reesei* RutC30 genomic DNA (isolated using a DNeasy Plant Maxi Kit, QIAGEN Inc., Valencia, Calif.), 0.3 µM primer 993429, 0.3 µM primer 993428, and 2 units of Vent polymerase (New England Biolabs, Beverly, Mass.). The reactions were incubated in an Eppendorf Mastercycler 5333 (Hamburg, Germany) programmed as follows: 30 cycles each for 30 seconds at 94° C., 30 seconds at 55° C., and 30 seconds at 72° C. (15 minute final extension). The reaction products were isolated on a 1.0% agarose gel using 40 mM Tris base-20 mM sodium acetate-1 mM disodium EDTA (TAE) buffer where a 229 bp product band was excised from the gel and purified using a QIAquick Gel Extraction Kit (QIAGEN Inc., Valencia, Calif.) according to the manufacturer's instructions.

Figure 2:
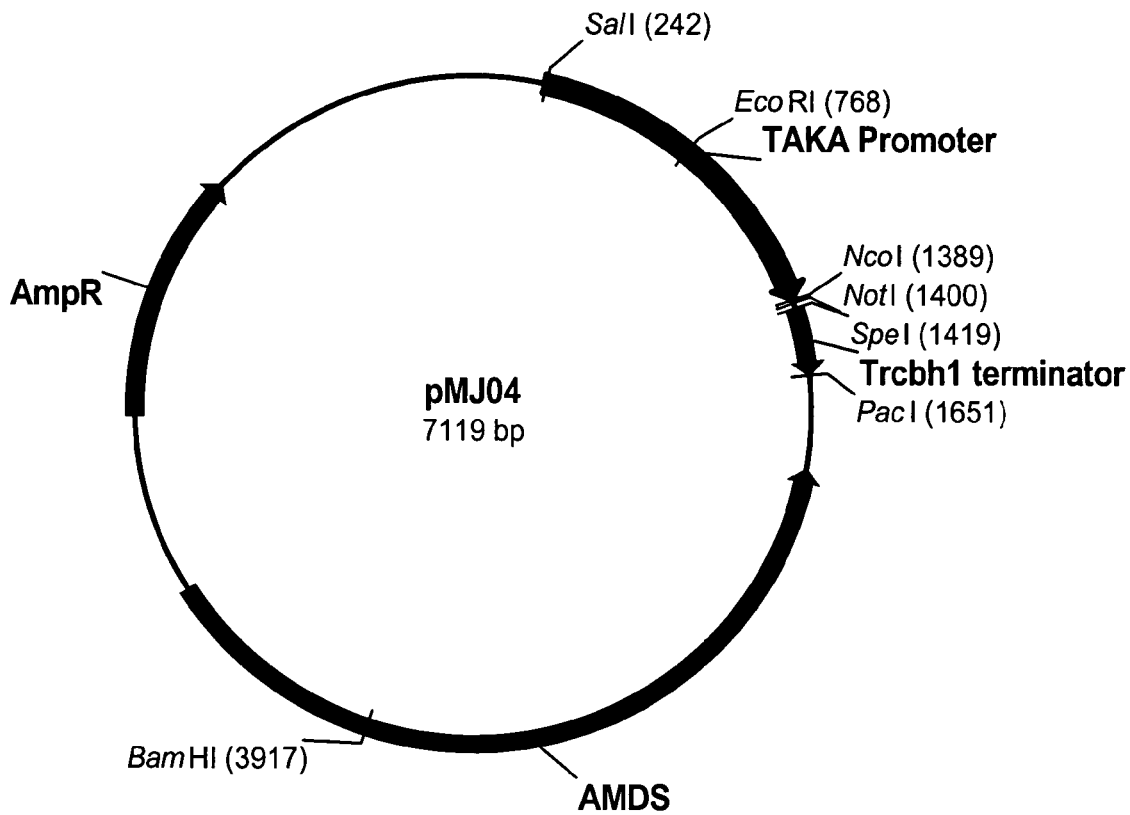
FIG. 2 shows a restriction map of pMJ04.

The resulting PCR fragment was digested with Pac I and Spe I and ligated into pAILo1 digested with the same restriction enzymes, using a Rapid Ligation Kit (Roche, Indianapolis, Ind.), to generate pMJ04 (FIG. 2).

Example 3

Construction of pMJ06 Expression Vector

Expression vector pMJ06 was constructed by first PCR amplifying the *Trichoderma reesei* Cel7A cellobiohydrolase 1 gene (cbh1) promoter from *Trichoderma reesei* RutC30 genomic DNA using primers 993696 (antisense) and 993695 (sense) shown below. The antisense primer was engineered to have a Sal I site at the 5'-end of the sense primer and an Nco I site at the 5'-end of the antisense primer.
Primer 993695 (Sense):

```
Primer 993695 (sense):
5'-ACTAGTCGACCGAATGTAGGATTGTT-3'      (SEQ ID NO: 10)
```

Primer 993696 (Antisense):

```
Primer 993696 (antisense):
5'-TGACCATGGTGCGCAGTCC-3'             (SEQ ID NO: 11)
```

The amplification reactions (50 µl) were composed of 1× ThermoPol Reaction Buffer, 0.3 mM dNTPs, 100 ng of *Trichoderma reesei* RutC30 genomic DNA (prepared using a DNeasy Plant Maxi Kit), 0.3 µM primer 993696, 0.3 µM primer 993695, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension). The reaction products were isolated on a 1.0% agarose gel using TAE buffer where a 988 bp product band was excised from the gel and purified using a QIAquick Gel Extraction Kit according to the manufacturer's instructions.

Figure 3:
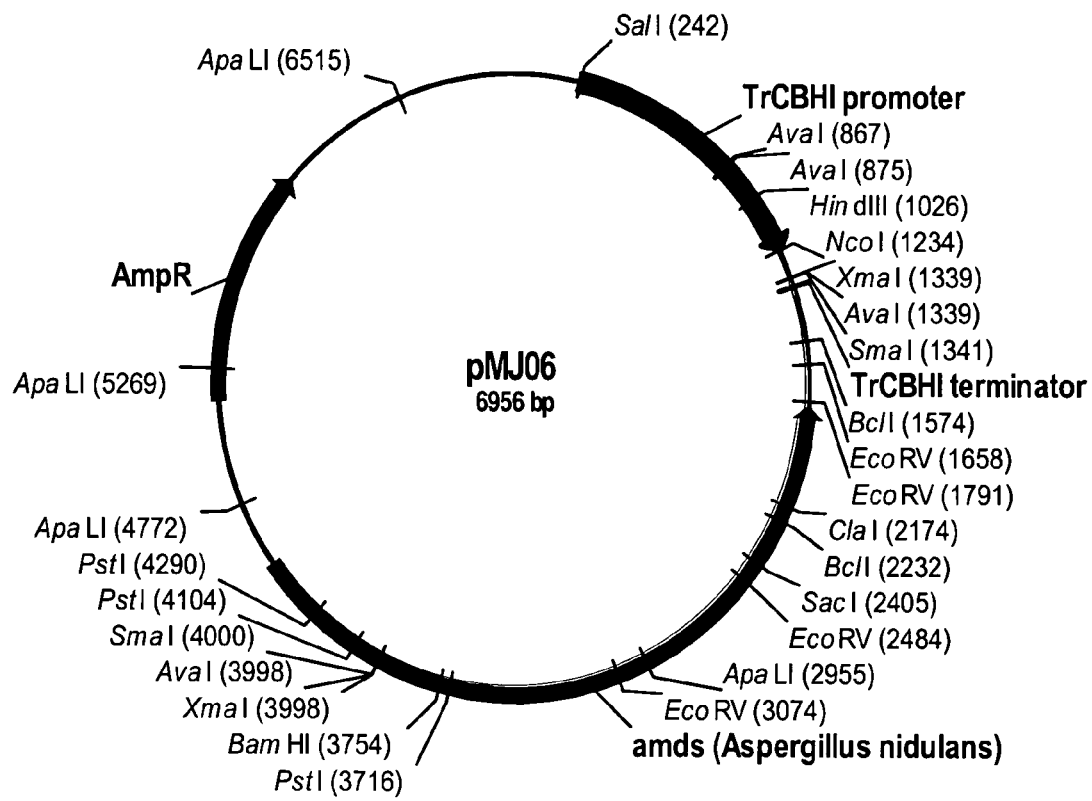
FIG. 3 shows a restriction map of pMJ06.

The resulting PCR fragment was digested with Nco I and Sal I and ligated into pMJ04 digested with the same restriction enzymes, using a Rapid Ligation Kit, to generate pMJ06 (FIG. 3).

Example 4

Construction of pMJ09 Expression Vector

Expression vector pMJ09 was constructed by PCR amplifying the *Trichoderma reesei* Cel7A cellobiohydrolase 1 gene (cbh1) terminator from *Trichoderma reesei* RutC30 genomic DNA using primers 993843 (antisense) and 99344 (sense) shown below. The antisense primer was engineered to have a Pac I and a Spe I sites at the 5'-end and a Pvu I site at the 5'-end of the sense primer.
Primer 993844 (Sense):

```
Primer 993844 (sense):
5'-CGATCGTCTCCCTATGGGTCATTACC-3'      (SEQ ID NO: 12)
```

Primer 993843 (Antisense):

```
Primer 993844 (sense):
5'-ACTAGTTAATTAAGCTCCGTGGCGAAAG-3'    (SEQ ID NO: 13)
```

The amplification reactions (50 µl) were composed of 1× ThermoPol Reaction Buffer, 0.3 mM dNTPs, 100 ng of *Trichoderma reesei* RutC30 genomic DNA (extracted using DNeasy Plant Maxi Kit), 0.3 µM primer 993844, 0.3 µM primer 993843, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension). The reaction products were isolated on a 1.0% agarose gel using TAE buffer where a 473 bp product band was excised from the gel and purified using a QIAquick Gel Extraction Kit according to the manufacturer's instructions.

Figure 4:
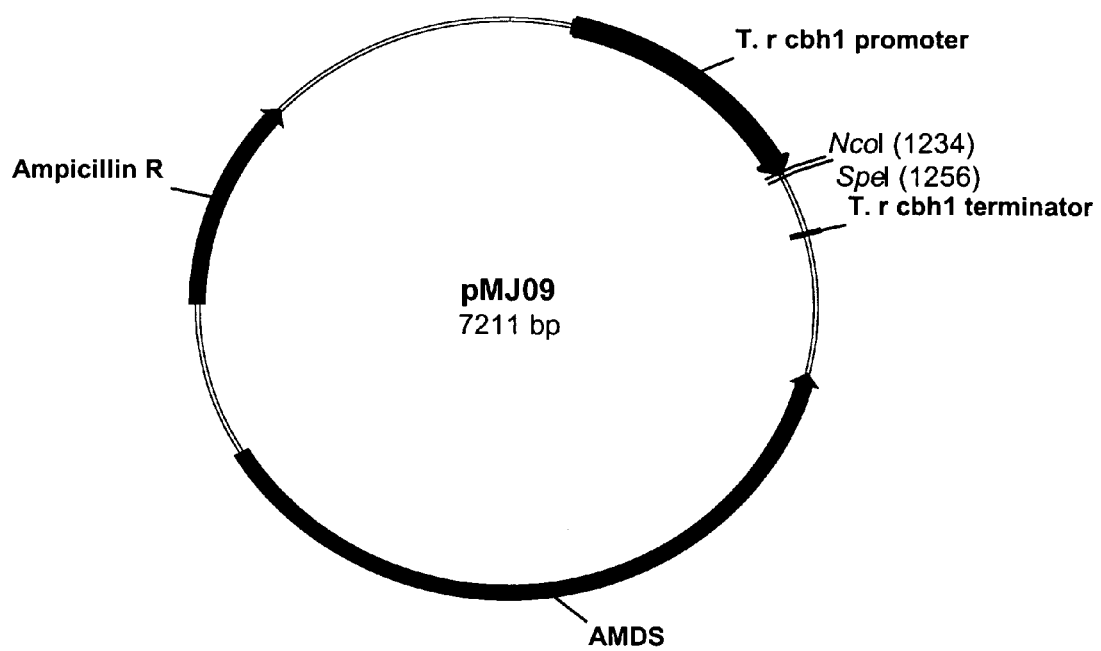
FIG. 4 shows a restriction map of pMJ09.

The resulting PCR fragment was digested with Pvu I and Spe I and ligated into pMJ06 digested with Pac I and Spe I, using a Rapid Ligation Kit, to generate pMJ09 (FIG. 4).

Example 5

Fermentation and Mycelial Tissue

*Trichoderma reesei* RutC30 was grown under cellulase inducing standard conditions as described by Mandels and Weber, 1969, *Adv. Chem. Ser.* 95: 391-413). Mycelial samples were harvested by filtration through Whatman paper and quick-frozen in liquid nitrogen. The samples were stored at −80° C. until they were disrupted for RNA extraction.

Example 6

Expressed Sequence Tags (ESTs) cDNA Library Construction

Total cellular RNA was extracted from the mycelial samples described in Example 5, according to the method of Timberlake and Barnard (1981, *Cell* 26: 29-37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions.

Double-stranded cDNA was synthesized using approximately 5 µg of poly(A)+ mRNA according to the method of Gubler and Hoffman (1983, *Gene* 25: 263-269), except a Not I-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.). BamH I/EcoR I adaptors were then ligated to the blunt ends of the cDNA. After digestion with Not I, the cDNA was size selected (ca. 0.7-4.5 kb) by 0.7% agarose gel electrophoresis using TAE buffer, and ligated with pYES2 (Invitrogen, Carlsbad, Calif.) which had been cleaved with Not I plus BamH I and dephosphorylated with calf-intestine alkaline phosphatase (Boehringer Mannheim Corporation, Indianapolis, Ind.).

The ligation mixture was used to transform competent *E. coli* TOP10 cells (Invitrogen, Carlsbad, Calif.) according to the manufacturer's instructions. Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) supplemented with ampicillin at a final concentration of 50 µg per ml.

Example 7

Template Preparation and Nucleotide Sequencing of cDNA Clones

From the cDNA library described in Example 6, approximately 7000 transformant colonies were picked directly from the 2YT plates into 96-well microtiter plates which contained 100 µl of 2YT broth supplemented with 50 µg of ampicillin per ml. The plates were incubated overnight at 37° C. with shaking at 200 rpm. After incubation, 100 µl of sterile 50% glycerol were added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of ampicillin per ml in each well. The primary microtiter plates were stored frozen at −80° C. The secondary deep-dish plates were incubated at 37° C. overnight with vigorous agitation (300 rpm) on a rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using a 96-well Miniprep Kit protocol of Advanced Genetic Technologies Corporation (Gaithersburg, Md.) as modified by Utterback et al. (1995, *Genome Sci. Technol.* 1: 1-8). Single-pass DNA sequencing was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and the T7 sequencing primer:

```
                                        (SEQ ID NO: 14)
T7 primer: 5'-TAATACGACTCACTATAGGG-3'
```

Example 8

Analysis of DNA Sequence Data of cDNA Clones

Nucleotide sequence data were scrutinized for quality and vector sequences and ambiguous base calls at the ends of the DNA sequences were trimmed, and all sequences were compared to each other with assistance of PHRED/PHRAP software (University of Washington, Seattle, Wash.). The resulting contigs and singletons were translated in six frames and searched against publicly available protein databases using GeneMatcher™ software (Paracel, Inc., Pasadena, Calif.) with a modified Smith-Waterman algorithm using the BLOSUM 62 matrix.

Example 9

Identification of cDNA Clones Encoding a Family 6 Cellobiohydrolase II (Cel6A)

Putative cDNA clones encoding a Family 6 cellobiohydrolase (Cel6A) were identified by comparing the deduced amino acid sequence of the assembled ESTs to protein sequences deposited in publicly available databases such as Swissprot, Genpept, and PIR. One clone, *Trichoderma reesei* EST Tr0749, was selected for nucleotide sequence analysis which revealed an 1747 bp pYES2 insert which contained a 1413 bp open reading-frame as shown in SEQ ID NO: 15 and a deduced amino acid sequence as shown in SEQ ID NO: 16. The plasmid containing *Trichoderma reesei* Cel6A cellobiohydrolase II was designated pTr0749.

Example 10

Construction of pSMai148 Expression Vector

Expression vector pSMai148 was constructed for transcription of double stranded-RNA (ds-RNA) derived from the *Trichoderma reesei* Cel6A cellobiohydrolase II gene and intended for the silencing of expression of the *Trichoderma reesei* Cel6A cellobiohydrolase II gene in *Trichoderma reesei* RutC30 strain. Plasmid pSMai148 was generated by PCR amplifying a 210 bp of the *Trichoderma reesei* Cel6A cellobiohydrolase II coding region from pTr0749 using primers 994991 (antisense) and 994990 (sense) shown below. The antisense primer was engineered to have an EcoR I site at the 5'-end and a Nco I site at the 5'-end of the sense primer.

Primer 994991 (Sense):

```
                                          (SEQ ID NO: 17)
Primer 994991 (antisense):
5'-GGAATTCTAGTTCTTATATTTGGCGACGCCACCATCT-3'
```

Primer 994990 (Sense):

```
                                          (SEQ ID NO: 18)
Primer 994990 (sense):
5'-CATGCCATGGAAAGGTTCCCTCTTTTATGTGGCTAG-3'
```

The amplification reactions (50 µl) were composed of 1× ThermoPol Reaction Buffer, 0.3 mM dNTPs, 10 ng of pTr0749, 0.3 µM primer 994990, 0.3 µM primer 994991, and 2.5 units of Taq polymerase (New England Biolabs, Beverly, Mass.). The reactions were incubated in an Eppendorf Mastercycler 5333 programmed as follows: 30 cycles each for 30 seconds at 94° C., 30 seconds at 55° C., and 30 seconds at 72° C. (15 minute final extension). The reaction products were isolated on a 1.0% agarose gel using TAE buffer where a 227 bp product band was excised from the gel and purified using a QIAquick Gel Extraction Kit according to the manufacturer's instructions.

A separate PCR was performed to amplify a 337 bp fragment of the *Trichoderma reesei* Cel6A cellobiohydrolase II coding region from pTr0749 using primers 994993 (antisense) and 994992 (sense) shown below. The antisense primer was engineered to have an EcoR I site at the 5'-end and a Pac I site at the 5'-end of the sense primer.

Primer 994993 (Sense):

```
                                          (SEQ ID NO: 19)
Primer 994993 (antisense):
5'-GGAATTCTGACTGAGCATTGGCACACTTTGGAGTAC-3'
```

Primer 994992 (Sense):

```
                                           (SEQ ID NO: 20)
  Primer 994992 (sense):
  5'-CCTTAATTAAAAAGGTTCCCTCTTTTATGTGGCTAG-3'
```

The amplification reactions (50 µl) were composed of 1× ThermoPol Reaction Buffer, 0.3 mM dNTPs, 10 ng of pTr0749, 0.3 µM primer 994992, 0.3 µM primer 994993, and 2.5 units of Taq polymerase. The reactions were incubated in an Eppendorf Mastercycler 5333 programmed as follows: 30 cycles each for 30 seconds at 94° C., 30 seconds at 55° C., and 30 seconds at 72° C. (15 minute final extension). The reaction products were isolated on a 1.0% agarose gel using TAE buffer where a 354 bp product band was excised from the gel and purified using a QIAquick Gel Extraction Kit according to the manufacturer's instructions.

Figure 5:
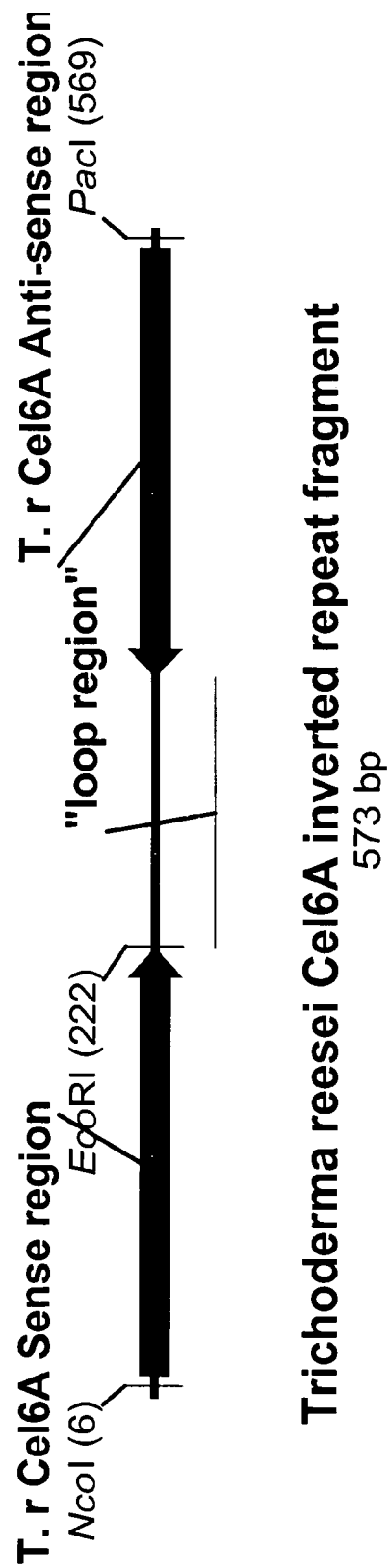
FIG. 5 shows a restriction map of a *Trichoderma reesei* Cel6A inverted repeat fragment.
Figure 6:
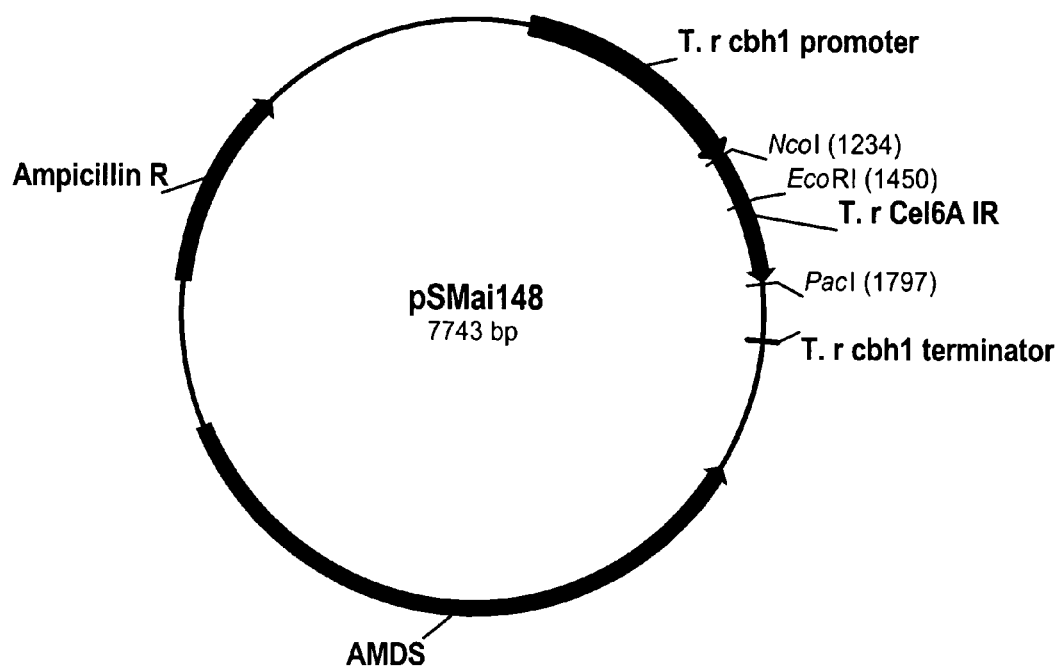
FIG. 6 shows a restriction map of pSMai148.

The resulting *Trichoderma reesei* Cel6A cellobiohydrolase II PCR fragment was digested with Pac I and EcoR I and ligated in an inverted orientation downstream of the Nco I and EcoR I digested *Trichoderma reesei* Cel6A cellobiohydrolase II PCR fragment (from first PCR). The tail-to-tail repeat (FIG. 5) was ligated into Pac I and Nco I digested pMJ09 vector, using T4 DNA ligase (Roche, Indianapolis, Ind.) according to manufacturer's protocol, to generate pSMai148 (FIG. 6).

Example 11

Transformation *Trichoderma reesei* with an Expression Construct Possessing an Inverted Repeat Fragment of the Cel6A Cellobiohydrolase II Gene To demonstrate that double stranded RNA-mediated (dsRNA) interference occurs in *Trichoderma reesei*, the pSMai148 expression vector, expressing the self-complementary hairpin RNA of the Cel6A cellobiohydrolase II sequence, was transformed into *Trichoderma reesei* RutC30 protoplasts. As a control, pMJ09 plasmid ("Empty vector") (FIG. 4), the parent vector of pSMai148, was also included. Both constructs contained the amdS gene providing selection for growth on acetamide as the sole nitrogen source and the *Trichoderma reesei* Cel6A cellobiohydrolase II sequence in the pSMai148 plasmid was placed under the control of the strong cellulose-inducible *Trichoderma reesei* Cel7A cellobiohydrolase 1 promoter.

Protoplast preparation and transformation was performed using a modified protocol by Penttila et al., 1987, *Gene* 61: 155-164. Briefly, *Trichoderma reesei* RutC30 was cultivated in 25 ml of YP medium, supplemented with 2% (w/v) glucose and 10 mM uridine, with gentle agitation (90 rpm) at 27° C. for 17 hours. Mycelia were collected by filtration using a Millipore Vacuum Driven Disposable Filtration System (Millipore, Bedford, Mass.) and washed twice with deionized water and twice with 1.2 M sorbitol. Protoplasts were generated by suspending the washed mycelia in 20 ml of 1.2 M sorbitol containing 15 mg of Glucanex® 200 G (Novozymes Switzerland AG, Neumatt, Switzerland) per ml and 0.36 units of chitinase (Sigma Chemical Co., St. Louis, Mo.) per ml for 15-25 minutes at 34° C. with gentle shaking (90 rpm). Protoplasts were collected by centrifuging for 7 minutes at 400×g and washed twice with cold 1.2 M sorbitol. The protoplasts were counted using a haemacytometer and re-suspended to a final concentration of $1 \times 10^8$ protoplasts/ml in STC. Excess protoplasts were stored in a Cryo 1° C. Freezing Container (Nalgene, Rochester, N.Y.) at −80° C.

Approximately 7 µg of Pme I digested expression plasmid (pSMai148 or pMJ09) was added to 100 µl of the protoplast solution and mixed gently. PEG buffer (250 µl) was added, mixed, and incubated at room temperature for 30 minutes. STC (3 ml) was then added, mixed, and plated onto COVE plates. The plates were incubated at 28° C. for 5-7 days. Transformants were sub-cultured onto COVE2 plates and grown at 28° C.

Example 12

Detection of *Trichoderma reesei* Cel6A Cellobiohydrolase II Protein by SDS-Polyacrylamide Gels Twenty transformants (SMA148-01 to SMA148-20) harboring the *Trichoderma reesei* Cel6A cellobiohydrolase II inverted repeat fragment and 10 transformants (MJ09-01 and MJ09-10) containing "Empty vector" were randomly selected and cultured in 125 ml baffled shake flasks containing 25 ml of cellulase-inducing medium at pH 6.0 inoculated with spores of the transformants and incubated at 28° C. and 200 rpm for 7 days. *Trichoderma reesei* RutC30 was run as a control. Culture broth samples were removed 7 days post-inoculation, centrifuged at 15,700×g for 5 minutes in a microcentrifuge, and the supernatants transferred to new tubes.

The extent of *Trichoderma reesei* Cel6A cellobiohydrolase II silencing was initially evaluated at a protein level by analyzing total broth on SDS-PAGE gels. SDS-PAGE was carried out using Criterion™ Tris-HCl gels (Bio-Rad Laboratories, Hercules, Calif.) with The Criterion™ Cell (Bio-Rad Laboratories, Hercules, Calif.). Five µl of day 7 samples were suspended in 2× concentration of Laemmli Sample Buffer (Bio-Rad Laboratories, Hercules, Calif.) and boiled for 3 minutes in the presence of 5% beta-mercaptoethanol. All the samples were loaded onto a polyacrylamide gel and subjected to electrophoresis in 1×Tris/Glycine/SDS running buffer (Bio-Rad Laboratories, Hercules, Calif.). The resulting gel was stained with Bio-Safe™ Coomassie Stain (Bio-Rad Laboratories, Hercules, Calif.).

SDS-PAGE analysis showed that the majority of the *Trichoderma reesei* RutC30 transformants carrying the *Trichoderma reesei* Cel6A cellobiohydrolase II inverted repeat fragment (SMA148-01 to SMA148-20) produced significantly lower amounts of *Trichoderma reesei* Cel6A cellobiohydrolase II protein compared to transformants harboring the "Empty vector" (pMJ09-01 to pMJ09-10). One transformant (transformant 14) exhibited complete lack of the protein.

Six SMA148 transformants (transformants 1, 2, 11, 12, 13, 14) showing varying degrees of *Trichoderma reesei* Cel6A cellobiohydrolase II protein reduction and two "Empty vector" transformants (MJ09-03 and MJ09-04) were selected for further analysis. Two rounds of single spore isolation were performed on these transformants to obtain pure strains. These single spore isolated transformants were grown in 25 ml of cellulase-inducing medium (pH 5.0) at 28° C. In addition, the host strain (*Trichoderma reesei* RutC30) and a positive control strain (*Trichoderma reesei* SaMe02) where the *Trichoderma reesei* Cel6A gene was knocked-out by homologous recombination was also cultured under the same conditions. Both supernatant and mycelia were collected from each of these samples at 3 days post-inoculation and submitted to SDS-PAGE analysis as described earlier.

SDS-PAGE showed that single-spore isolation further decreased the level of *Trichoderma reesei* Cel6A cellobiohydrolase II produced, presumably due to the transformants becoming more homozygous as a result of spore purification.

Example 13

Detection of *Trichoderma reesei* Cel6A Cellobiohydrolase II mRNA by Northern Blots Northern hybridization was conducted to determine if incorporation of *Trichoderma reesei* Cel6A cellobiohydrolase II inverted repeat fragment (pSMai148) in a strain resulted in a reduction in the amount of *Trichoderma reesei* Cel6A cellobiohydrolase II mRNA. Total RNA was extracted from frozen mycelia obtained in Example 11 using Fenozol™ (Active Motif, Carlsbad, Calif.) and following a slightly modified protocol by the manufacturer. Briefly, frozen mycelia were ground to a fine powder in an electric coffee grinder with a few chips of dry ice. The ground mycelia were mixed with 20 ml of Fenozol™, vortexed, and incubated in a 50° C. water-bath for 15 minutes, after which 5 ml of chloroform (Sigma, St. Louis, Mo.) was added, vortexed, and allowed to stand at room temperature for 10 minutes. The samples were then centrifuged at 700×g at room temperature for 20 minutes and the aqueous phase transferred to a new tube and an equal volume of phenol-chloroform-isoamylalcohol was added. The samples were vortexed and centrifuged for 10 minutes at 700×g and the top aqueous layer was added to an equal volume of chloroform. The samples were further centrifuged for 10 minutes at 700×g and the aqueous layer was transferred to a tube containing 0.5 ml of 3 M sodium acetate pH 5.2 and 6.25 ml of isopropanol. The samples were mixed, incubated at room temperature for 15 minutes, and centrifuged at 13400×g for 30 minutes to recover RNA. The RNA was washed with 70% ethanol, centrifuged, dried, and re-suspended in DEPC-water. The quantity and quality of the extracted RNA were assessed on an Agilent 2100 Bioanalyzer (Agilent Technologies, Wilmington, Del.) in conjunction with the RNA 6000 Nano LabChip® Kit (Agilent Technologies, Wilmington, Del.) according to manufacturer's protocol.

Isolated total RNA was fractionated by electrophoresis for 4-6 hours on a 1% agarose/formaldehyde gel and blotted onto Nytran SuperCharge membrane (Schleicher & Schuell BioScience, Keene, N.H.) using a Turboblotter (Schleicher & Schuell BioScience, Keene, N.H.) for 14-16 hours, following the manufacturer's recommendations. The membrane was first hybridized with a 505 bp digoxigenin-labeled *Trichoderma reesei* Cel6A cellobiohydrolase II probe, which was synthesized by incorporation of digoxigenin-11-dUTP during PCR using primers 996118 (antisense) and 996117 (sense) shown below:
Primer 996118 (Antisense):

```
Primer 996118 (antisense):
5'-AAATCGTGGCGCACTGCTGT-3'        (SEQ ID NO: 21)
```

Primer 996117 (Sense):

```
(Primer 996117) (sense):
5'-TGAGTGCATCAACTACGCCG-3'        (SEQ ID NO: 22)
```

The amplification reaction (50 µl) was composed of 1× ThermoPol Reaction Buffer, 5 µl of PCR DIG Labeling Mix (Roche Molecular Biochemicals, Indianapolis, Ind., USA), 10 ng of pTr0749, 0.3 µM primer 996118, 0.3 µM primer 996117, and 2.5 units of Taq polymerase. The reactions were incubated in an Eppendorf Mastercycler 5333 programmed as follows: 30 cycles each for 30 seconds at 94° C., 30 seconds at 50° C., and 30 seconds at 72° C. (15 minute final extension). Five microliters of the PCR product was size-selected on 1.5% agarose gels using TAE buffer, stained with ethidium bromide, and visualized under a UV transilluminator. Incorporation of digoxigenin was indicated by increase in molecular mass.

Hybridization was performed in DIG Easy Hyb buffer (Roche Molecular Biochemicals, Indianapolis, Ind., USA) at 50° C. for 15-17 hours. The membrane was then washed under high stringency conditions in 2×SSC plus 0.1% SDS for 5 minutes at room temperature followed by two washes in 0.1×SSC plus 0.1% SDS for 15 minutes each at 50° C. The probe-target hybrids were detected by chemiluminescent assay (Roche Molecular Biochemicals, Indianapolis, Ind.) following the manufacturer's instructions. The membrane was then stripped in 50% formamide/5% SDS/50 mM Tris-HCl, pH 7.5 at 80° C. for 2 hours and re-probed with a 407 bp digoxigenin-labeled probe encoding the *Trichoderma reesei* actin 1 gene (Accession Number X75421) (Matheucci et al., 1995, *Gene* 161: 103-106) prepared using the exact same conditions as before. The 407 bp actin 1 gene probe was synthesized by incorporation of digoxigenin-11-dUTP during PCR using primers 996120 (antisense) and 996119 (sense) shown below.
Primer 996120 (Antisense):

```
Primer 996120 (antisense):
5'-GTCAACACGACGAATGGCGT-3'        (SEQ ID NO: 23)
```

Primer 996119 (Sense):

```
Primer 996119 (sense):
5'-TGATCGGTATGGGTCAGAAGG-3'       (SEQ ID NO: 24)
```

The amplification reaction (50 µl) was composed of 1× ThermoPol Reaction Buffer, 5 µl of PCR DIG Labeling Mix (Roche, Indianapolis, Ind.), 100 ng *Trichoderma reesei* RutC30 genomic DNA, (isolated using a DNeasy Plant Maxi Kit), 0.3 µM primer 996119, 0.3 µM primer 996120, and 2.5 units of Taq polymerase. The reactions were incubated in an Eppendorf Mastercycler 5333 programmed as follows: 30 cycles each for 30 seconds at 94° C., 30 seconds at 50° C., and 30 seconds at 72° C. (15 minute final extension).

Five microliters of the PCR product was size-selected on 1.5% agarose gels using TAE buffer, stained with ethidium bromide, and visualized under a UV transilluminator. Incorporation of digoxigenin was indicated by increase in molecular mass.

The Northern showed that transformants which had the *Trichoderma reesei* Cel6A cellobiohydrolase II inverted repeat sequences produced substantially less *Trichoderma reesei* Cel6A cellobiohydrolase II transcripts compared with transformants that received the "Empty vector" (negative control) and the host strain (*Trichoderma reesei* RutC30). This result was particularly noticeable in transformants 11 and 14 where the *Trichoderma reesei* Cel6A cellobiohydrolase II mRNAs were not detectable although actin 1 gene transcripts (actin 1 was used as a control for equivalent RNA loading) were clearly present. The apparent 100% suppression in *Trichoderma reesei* Cel6A cellobiohydrolase II mRNA correlated strongly with the 100% reduction in the *Trichoderma reesei* Cel6A cellobiohydrolase II protein in these transformants, indicating that RNA interference in *Trichoderma* resulted from a reduction in the amount of target mRNA available for translation.

Example 14

Detection of *Trichoderma reesei* Cel6A Cellobiohydrolase II mRNA by Real-Time Reverse-Transcription-PCR The relative expression levels of *Trichoderma reesei* Cel6A cellobiohydrolase II mRNA in the different transformants were quantitated with real-time Reverse Transcription-PCR (RT-PCR). Total RNA was extracted from each transformant as described in Example 13 to serve as a template for RT-PCR reactions. The *Trichoderma reesei* actin 1 gene was used as an internal control. Primers were designed using Primer Express™ software (Applied Biosystems, Foster City, Calif.). After primer lists were generated according to favorability ratings, pairs were chosen by selecting the first set of primers that had no more than two G+C in the last 5 bases at the 3'-end. The following primers were used:
*Trichoderma reesei* Cel6A Cellobiohydrolase II Forward Primer (996006):

```
Trichoderma reesei Cel6A
cellobiohydrolase II
forward primer (996006):
5'-CTGGTCCAACGCCTTCTTCAT-3'    (SEQ ID NO: 25)
```

*Trichoderma reesei* Cel6A Cellobiohydrolase II Reverse Primer (996007):

```
Trichoderma reesei Cel6A
cellobiohydrolase II
reverse primer (996007):
5'-GGAACGTAGTGAGGCTCGCTAA-3'   (SEQ ID NO: 26)
```

*Trichoderma reesei* Actin 1 Forward Primer (996121):

```
Tricoderma reesei actin
1 forward primer (996121):
5'-CATGGCTGGTCGTGATCCTTACC-3'  (SEQ ID NO: 27)
```

```
5'-CCTTGATGTCACGGACGATTTC-3'   (SEQ ID NO: 28)
```

The RT-PCR assay was performed using an ABI Prism® 7700 System (Applied Biosystems, Foster City, Calif.) and SYBR® Green PCR master mix (Applied Biosystems, Foster City, Calif.). Each reaction mixture contained 12.5 µl of SYBR® Green PCR Master Mix, 6 units of SuperscriptII (Invitrogen, Carlsbad, Calif.), 0.83 µM forward primer, 0.83 µM reverse primer, and varying concentrations of RNA template in a total volume of 25 µl. Reverse transcription was performed for 30 minutes at 50° C., followed by inactivation of SuperscriptII and activation of AmpliTaq® at 95° C. for 10 minutes. Forty PCR cycles were carried out under the following conditions: 15 seconds of denaturation at 95° C. followed by 1 minute at 60° C. for annealing and extension. Each sample was prepared in triplicate. A negative control with no SuperscriptII was run on every plate tested to assess specificity. Furthermore, since SYBR® Green binds non-specifically to double stranded-DNA, an aliquot of the PCR amplification products was electrophoresed on a 2.0% agarose gel using TAE buffer to confirm the absence of non-specific amplification.

Data obtained from the ABI PRISM 7700 Sequence Detection System was analyzed using "Standard Curve Method for Relative Quantitation" as described in ABI user Bulletin #2 (Applied Biosystems, Foster City, Calif.). In this method, the quantity of expression of treated sample was calculated relative to the untreated control sample. The quantity of the treated sample was determined from the standard curve and divided by the quantity of the untreated control sample. Thus, the untreated sample was designated the 1× sample, and all other quantities were expressed as an n-fold difference relative to the untreated sample. Then, the treated sample amount was normalized to an endogenous control, actin 1, to account for differences in the amount of total RNA added to each reaction.

Figure 7:
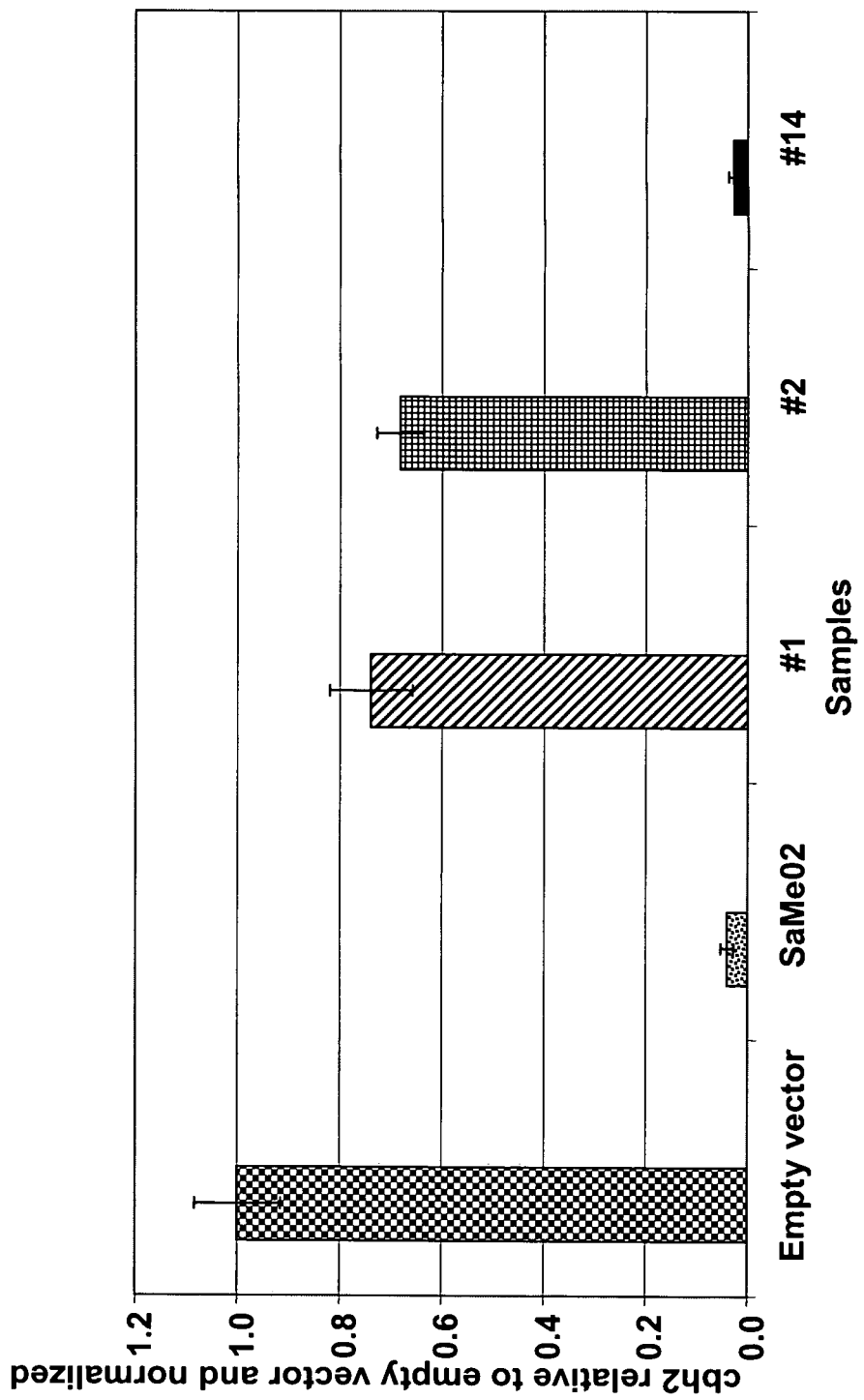
FIG. 7 shows the relative expression level of *Trichoderma reesei* Cel6A cellobiohydrolase II mRNA in transformant 14, a positive control-strain (*Trichoderma reesei* SaMe02), and the "Empty vector control" in shake flasks.

FIG. 7 shows that the relative expression level of *Trichoderma reesei* Cel6A cellobiohydrolase II mRNA was lowest in transformant 14 and the positive control strain (SaMe02) when compared to the "Empty vector control", correlating strongly with the Northern hybridization data.

Example 15

Construction of a Subtracted and Normalized cDNA Library from *Trichoderma reesei* Using Suppression Subtractive Hybridization (SSH)

*Trichoderma reesei* strain RutC30 was grown in two-liter Applikon laboratory fermentors using a base Celluclast™ medium and fermentation conditions. The carbon sources included glucose, cellulose, or pre-treated and washed corn stover. All were loaded based on the carbon equivalent of 52 g of glucose per liter. The fermentation method employed a temperature of 28° C., pH 4.5, and a growth time of approximately 120 hours. In addition to the carbon source, all fermentations contained per liter the following medium components: 5 g of glucose, 10 g of corn steep solids, 2.08 g of $CaCl_2$, 3.87 g of $(NH_4)_2SO_4$, 2.8 g of $KH_2PO_4$, 1.63 g of $MgSO_4.7H_2O$, 0.75 ml of trace metals, and 1.8 ml of pluronic acid. The trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. Samples of mycelia were harvested one, two, three, four, and five days post-inoculum and were quickly separated from the culture medium by filtration through Miracloth™ (Calbiochem, La Jolla, Calif.), frozen in liquid nitrogen, and stored at −80° C.

Total cellular RNA was isolated from frozen cells grown on glucose, cellulose, or pre-treated corn stover (Example 1) using slight modifications to the method of Timberlake and Barnard, 1981, supra. RNA extraction buffer was prepared by adding a freshly prepared solution of p-aminosalicylic acid (9.6 g in 80 ml of DEPC-treated water) to a solution of triisopropylnaphthalene sulfonic acid (1.6 g in 80 ml of DEPC-treated water). This mixture was added to 40 ml of 5×RNB solution (1 M Tris-HCl, pH 8.5, 1.25 M NaCl, 0.25 M EGTA) with stirring. Frozen mycelia were ground to a fine powder in an electric coffee grinder with a few chips of dry ice. The ground mycelia were poured directly into 20 ml of RNA extraction buffer on ice, and an equal volume of TE-saturated phenol was added. After vigorous agitation, the samples were centrifuged at 2500 rpm (Sorvall RT7 centrifuge equipped with a H1000B rotor) for 10 minutes to separate phases. The aqueous phase was transferred to a new tube that contained 10 ml of phenol and 10 ml of chloroform-isoamyl alcohol (24:1), while an additional 5 ml of extraction buffer was added to the phenol phase. The latter mixture was incubated at 68° C. for 5 minutes to liberate RNA trapped in polysomes and in the interface material. Following the incubation, the tubes were centrifuged at 2500 rpm (Sorvall RT7 centrifuge equipped with a H1000B rotor) for 10 minutes and the aqueous phase was combined with that obtained from the first extraction. These mixtures were subjected to repeated extraction with phenol-chloroform until there was no longer protein at the interface (usually five or six times). The RNA was recovered by centrifugation (30 minutes at 12,000×g) following precipitation with 0.3 M sodium acetate pH 5.2 and 50% isopropanol. From each sample consisting of approximately 1-2 grams of frozen mycelia generated in laboratory-scale fermentors, 0.4-1.8 mg of total cellular RNA was obtained.

The quality of RNA from cultures grown on cellulose and PCS was appraised by formaldehyde-agarose gel electrophoresis followed by Northern blotting and hybridization (Thomas, 1980, *Proc. Nat. Acad. Sci. USA* 77: 5201-5205) with a *Trichoderma reesei* cbh1 specific probe. The cbh1 probe fragment was amplified by standard PCR methods based on the published nucleotide sequence information available from the EMBL database (accession number E00389). The probes were labeled with horseradish peroxidase (HRP) and hybridized at 55° C. using the buffers and protocols provided in a North2South Direct HRP Labeling and Detection Kit (Pierce, Rockford, Ill.). The blots were washed three times in 2×SSC with 0.1% SDS at 55° C. for five minutes each, followed by three additional washes in 2×SSC (no SDS) for five minutes each. Following exposure of the blot to X-ray film, it was clear that virtually all of the hybridization signal in each lane was contained in a 1.8 kb cbh1 mRNA species that migrated to a position just slightly above the 18S ribosomal RNA band. There was no evidence of significant mRNA degradation on either the autoradiogram or on the ethidium bromide stained gel. Polyadenylated (polyA+) mRNA fractions were purified using an Oligotex™ mRNA Isolation Kit according to the manufacturer's instructions (QIAGEN, Valencia, Calif.). Yields of polyA+ mRNA from each of these samples ranged from 2 µg to 25 µg. Each of the mRNA fractions was subsequently analyzed by Northern blot hybridization using HRP-labeled probes derived from the *Trichoderma reesei* γ-actin and cbh1 genes. The γ-actin probe fragment was amplified by standard PCR methods and the following gene-specific primers.

5'-CCAGACATGACAATGTTGCCGTAG-3'    (SEQ ID NO: 29)

5'-TTTCGCTCTTCCTCACGCCATTG-3'    (SEQ ID NO: 30)

As expected, the hybridization signals were localized in bands that corresponded to the γ-actin and cbh1 mRNAs (ca. 1.2 kb and 1.8 kb, respectively) in each lane, indicating that the mRNA samples were of high quality and suitable for cDNA synthesis.

The suppression subtractive hybridization (SSH) method described by Diatchenko et al., 1996, supra, was used to generate a cDNA pool from *Trichoderma reesei* RutC30 that was both enriched for cellulose- and PCS-induced sequences and normalized to aid in recovery of rare transcripts. Table 1 below lists the combinations of driver and tester cDNAs used for these experiments.

TABLE 1

Driver and tester cDNA pools used for SSH.

| SSH Reaction | Driver cDNA source | Tester cDNA source |
| --- | --- | --- |
| 1 | Glucose-grown cells | PCS-grown cells |
| 2 | Glucose-grown cells | Cellulose-grown cells |
| 3 | Cellulose-grown cells | PCS-grown cells |

The resulting cDNA pools from the SSH reactions in Table 1 were used to generate subtractive libraries of cellulose- and PCS-induced sequences. For synthesis of cDNA, 400 ng of polyA+ mRNA derived from each time point (1-5 days) was combined for a total of 2 µg of template. Synthesis and subtraction of cDNA was done using a PCR-Select™ Kit (Clontech, Palo Alto, Calif.). The methods are based on the procedure of suppression subtractive hybridization (SSH) as outlined by Diatchenko et al., 1996, supra. The overall scheme is shown in FIG. 1. First, mRNA was converted from three separate fermentations of *Trichoderma reesei* RutC30 grown on glucose, cellulose, and PCS into double-stranded cDNA using reagents supplied with the PCR-Select™ Kit (Clontech, Palo Alto, Calif.). The differentially expressed cDNAs were present in both the "tester" cDNA pool (i.e., from cells grown on cellulose or corn stover) and the "driver" cDNA, but were present at much lower levels in the "driver" pool (Table 1). Both of these cDNA pools were digested with the restriction enzyme Rsa I which recognizes a four-base pair palindrome and yields blunt-end fragments (GT|AC). The tester cDNA pool was then divided into two samples and ligated with two different adaptor oligonucleotides (provided with the Clontech PCR-Select™-Kit) resulting in two populations of tester cDNA. The adaptors were designed without 5'-phosphate groups such that only the longer strand of each adaptor could be covalently linked to the 5'-ends of the cDNA.

In the first of two hybridizations using conditions specified in the Clontech PCR-Select™ Kit an excess of driver cDNA was added to each portion of tester cDNA. The mixtures were denatured by heating to 95° C. then allowed to anneal. Four types of molecules were generated by this annealing (designated as a, b, c, and d molecules). Type a molecules included equal concentrations of high- and low-abundance cDNAs, because the second-order kinetics of hybridization were faster for more abundant molecules in the pool which preferentially formed b type molecules. At the same time, type a molecules were significantly enriched for differentially expressed (e.g., cellulose- or PCS-induced) sequences, since common non-target cDNAs formed type c molecules with the driver. In a second hybridization, the two pools of primary hybridized products were combined so that the type a molecules from each tester sample could associate and form new type e hybrids. These were double-stranded tester molecules with different adaptor sequences on each end. Fresh denatured driver cDNA was also added to further enrich the pool of e molecules for differentially expressed sequences.

In the final step of the SSH procedure, the differentially expressed cDNAs were selectively amplified by PCR (conditions specified in the PCR-Select™ Kit) Only type e molecules that have two different primer annealing sites were amplified exponentially.

As a quality check, the cDNA clones from approximately 360 randomly picked colonies were purified by rolling circle amplification using an Amersham TempliPhi Kit and analyzed by DNA sequencing (70 from Reaction 1, 96 from Reaction 2, and 192 from Reaction 3). Clustering of the sequences using Transcript Assembler™ software (Paracel, Inc., Pasadena, Calif.) showed that each pool contained a high percentage of non-redundant clones—76% for Reaction 1, 90% for Reaction 2, and 67% for Reaction 3. In addition, the contigs (overlapping sequences of the same cDNA) identified in this analysis contained on average only two sequences. Collectively, these observations suggested that efficient normalization of the libraries was achieved during the SSH reactions, yielding a low level of redundancy in the corresponding cDNA libraries. These differentially expressed sequences were greatly enriched in the final subtracted cDNA pool, and useful as a hybridization probe or to create a subtractive library.

Subtracted and normalized cDNA fractions generated by the SSH procedure were ligated with pCRII-TOPO (Invitrogen, Carlsbad, Calif.) and the ligation mixtures were used to transform electrocompetent *E. coli* TOP10 cells (Invitrogen, Carlsbad, Calif.). Transformants were selected on LB agar plates (Miller, J. H. 1992. A short course in bacterial genetics. A laboratory manual and handbook for *Escherichia coli* and related bacteria. Cold Spring Harbor Press, Cold Spring Harbor, N.Y.) that contained 250 µg/ml X-Gal (no IPTG) and ampicillin at a final concentration of 100 µg/ml.

In order to evaluate the efficiency of subtraction and normalization in SSH cDNA libraries, two approaches were used: colony hybridization and sequencing of random clones from each SSH library. The procedure for colony hybridization is detailed in Birren et al. 1998. *Genome Analysis, A Laboratory Manual*, Vol. 2, Cold Spring Harbor Press, Cold Spring Harbor, N.Y.). Colony-hybridization analysis included approximately 700 independent clones from each subtracted [PCS minus glucose (SG), cellulose minus glucose (CG), PCS minus cellulose (SC)] and un-subtracted (cellulose, PCS) cDNA libraries with DIG-labeled cbh1 probe (abundant transcript), and γ-actin probe, a moderately abundant transcript representing a house-keeping gene (Table 2).

TABLE 2

Colony hybridization of SSH libraries probed with cbh1 and γ-actin cDNA fragments.

| Library | Frequency cbh1 | Frequency γ-actin |
|---|---|---|
| Cellulose (no SSH) | 3.3% | <0.17% |
| PCS (no SSH) | 3.7% | 0.13% |
| PCS minus glucose | 0.4% | ND |
| Cellulose minus glucose | 0.5% | ND |
| PCS minus cellulose | 0.1% | ND |

ND, not detected.

While the cbh1 was a rather abundant in the non-subtracted cellulose and PCS libraries (3.3% and 3.6% correspondingly), the subtracted SG and CG libraries contained almost 10 times less cbh1 clones, which indicated that the abundant transcript was successfully normalized. Colony-hybridization of the SC library showed very low occurrence of cbh1 (only 0.1% of cbh1 clones) indicating an efficient subtraction of this abundant transcript when performing SSH with cell populations both expressing high levels of cbh1.

The cDNA clones from approximately 360 randomly picked colonies were purified by rolling circle amplification (RCA) (Dean et al., 2001, *Genome Res.* 11: 1095-1099) and analyzed by DNA sequencing (70 from Reaction 1, 96 from Reaction 2, and 192 from Reaction 3). Clustering of the sequences using Transcript Assembler™ software showed that each pool contained a high percentage of non-redundant clones: 76% for reaction 1, 90% for reaction 2, and 67% for reaction 3. In addition, the contigs (overlapping sequences of the same cDNA) identified in this analysis contained on the average only two sequences. Collectively, these observations suggested that efficient normalization of the libraries was achieved during the SSH reactions, yielding a low level of redundancy in the corresponding cDNA libraries.

Example 16

Fabrication and Use of DNA Microarrays

A total of 3,608 white and light blue colonies were picked from the subtracted and normalized cDNA library described in Example 15. These were grown overnight in LB medium supplemented with 100 µg of ampicillin per ml in 96-well plates, and frozen at −80° C. Rolling circle amplification (Dean et al., 2001, *Genome Res.* 11: 1095-1099) of plasmid DNA from frozen cells was done using TempiPhi™ reagents from Amersham (Arlington Heights, Ill.). High-throughput processing of these reactions was performed using a Beckman Biomek® Fx robot (Beckman Coulter, Inc., Fullerton, Calif.) according to the manufacturer's instructions. The amplified and diluted genomic clones were then spotted from 384-well plates onto poly-L-lysine coated glass microscope slides using the equipment and methods described by Eisen and Brown, 1999, *Methods Enzymol.* 303: 179-205.

Example 17

Analysis of *Trichoderma reesei* Strains that Contain Gene Silencing Vectors

The RNA profiles of several *Trichoderma reesei* strains were compared as shown in Table 3 below. Fluorescent probes were prepared by reverse transcription of total RNA, incorporating aminoallyl-dUTP into first strand cDNA (total RNA was prepared using Fenozol reagents that are available commercially from Active Motif, Carlsbad, Calif.). The amino-cDNA products were subsequently labeled by direct coupling to either Cy3 or Cy5 monofunctional reactive dyes (Amersham, Arlington Heights, Ill.) and purified as described previously (Berka et al., 2003, *Proc. Nat. Acad. Sci. USA* 100: 5682-5687). Cy3 and Cy5 labeled probes were combined, purified and dried under a vacuum, resuspended in 15.5 µl of water, and combined with the following: 3.6 µl of 20×SSC, 2.5 µl of 250 mM HEPES (pH 7.0), 1.8 µl of poly-dA (500 µg/ml), and 0.54 µl of 10% SDS. Before hybridization, the solution was filtered with a 0.22 µm filter, heated to 95° C. for 2 minutes, and cooled to room temperature. The probe was applied to the microarray under a cover glass, placed in a humidified chamber, and incubated at 63° C. overnight (15-16 hours). Before scanning, the arrays were washed consecutively in 1×SSC with 0.03% SDS, 0.2×SSC, and 0.05×SSC and centrifuged for 2 minutes at approximately 100×g to remove excess liquid.

Microarray slides were imaged using an Axon 4000B scanner (Molecular Devices Corp., Sunnyvale, Calif.) according to the manufacturer's instructions. Fluorescence intensity values for microarray spots were measured, and the ratio of Cy5 to Cy3 (650 nm:532 nm) intensity for each spot was calculated following background subtraction. Those spots for which the intensity ratio varied by more than two-fold from unity were deemed to be differentially expressed.

TABLE 3

*Trichoderma reesei* RNA pools compared using DNA microarrays.

| Experiment Number | Cy3-label | Comment | Cy5-label | Comment |
|---|---|---|---|---|
| 1 | SMA148-11-1-3 | Total RNA isolated from a strain harboring a gene silencing vector to inhibit cbh2 mRNA | MJO9-4 (Empty vector) | Total RNA isolated from a control strain harboring an empty vector |

TABLE 3-continued

Trichoderma reesei RNA pools compared using DNA microarrays.

| Experiment Number | Cy3-label | Comment | Cy5-label | Comment |
|---|---|---|---|---|
| 2 | SaMe02 | Total RNA isolated from a cbh2-deleted strain | MJO9-4 (Empty vector) | Total RNA isolated from a control strain harboring an empty vector |
| 3 | SaMe02 | Total RNA isolated from a cbh2-deleted strain | SMA148-11-1-3 | Total RNA isolated from a strain harboring a gene silencing vector to inhibit cbh2 mRNA |

In experiments 1 and 3, a total of 72 spots were identified that satisfied the criterion of two-fold change in their fluorescence intensity ratios, and were therefore classified as differentially expressed sequences. DNA sequence analysis revealed that 63/72 (88%) corresponded to cbh2-specific transcripts. The remaining 9 spots corresponded to unknown or hypothetical gene sequences. It was possible that these may contain nucleotide sequences that are closely related to cbh2 and may encode conserved modules such as cellulose binding domains. In contrast to what was expected, the cbh2-mRNA levels in strains harboring the gene silencing vector appeared to be elevated compared to the corresponding mRNA levels in the control strain. This observation reflected the fact that the gene silenced transcript itself can hybridize to the cbh2 targets on the arrays, thereby giving the illusion that cbh2-specific mRNA levels were increased in the gene silencing strains. Nevertheless, the effect of gene silencing in *Trichoderma reesei* appeared to be highly specific in that there were few (if any) transcripts/genes other than cbh2 that were affected.

In experiment 2, none of the sequences on the microarrays appeared to be differentially expressed indicating that cbh2-specific RNA sequences were still produced by the cbh2-deleted strain at levels comparable to the control strain. It should be noted, however, that this presumably reflected the fact that the deletion/disruption event in *Trichoderma reesei* SaMe02 did not remove the entire coding region for cbh2. Thus, it was possible for the strain to make truncated transcripts that still hybridized to cbh2 targets on the microarrays.

Example 18

RNAi During Small-Scale Fermentation

Two-liter fermentations were performed as described in Example 5 on transformants 11 and 14, which showed almost 100% reduction for cbh2 mRNA, to determine whether gene silencing is successfully maintained throughout small-scale fermentations. Fermentations were also performed on the host strain *Trichoderma reesei* RutC30 and a positive control strain *Trichoderma reesei* SaMe02 where the cbh2 gene was knocked-out by homologous recombination. The level of cellobiohydrolase II protein was measured by SDS-PAGE analysis as described in Example 12.

The level of cellobiohydrolase II protein was substantially reduced in transformants 11 and 14, and *Trichoderma reesei* SaMe02, when compared to the host strain *Trichoderma reesei* RutC30.

Example 19

Detection of Small Interfering RNA of *Trichoderma reesei* Cel6A Cellobiohydrolase II by Northern Blot Hybridization Northern analysis was performed to examine transformants 1, 2, 11, 12, 13, and 14 for the presence or absence of *Trichoderma reesei* Cel6A cellobiohydrolase II-specific small interfering RNA (siRNA). The same total RNA that was used in Example 13 was used for this experiment. Isolated total RNA (25 µg) was mixed with 1 part TBE-Urea sample buffer (Bio-Rad Laboratories, Hercules, Calif.), heated for 15 minutes at 65° C., and fractionated by electrophoresis on a Criterion™ 15% polyacrylamide-7M urea gel (Bio-Rad Laboratories, Hercules, Calif.) with a Criterion™ Cell in 1×TBE running buffer (Bio-Rad Laboratories, Hercules, Calif.). RNA was then electroblotted to a Zeta-Probe® GT blotting membrane (Bio-Rad Laboratories, Hercules, Calif.) using a Criterion™ Blotter (Bio-Rad Laboratories, Hercules, Calif.) for an hour at 50V in 0.5×TBE transfer buffer (Bio-Rad Laboratories, Hercules, Calif.). After the transfer, RNA was fixed onto the membrane in a Stratalinker® 1800 UV Crosslinker (Stratagene, La Jolla, Calif.) using Auto-Crosslink setting. The membrane was hybridized with a 363 bp digoxigenin-labeled *Trichoderma reesei* Cel6A cellobiohydrolase II single stranded RNA probes, which was synthesized by in vitro transcription of *Trichoderma reesei* Cel6A cellobiohydrolase II template DNA in the presence of digoxigenin-11-dUTP using a DIG RNA Labeling Kit (Roche, Indianapolis, Ind.), following a protocol supplied by the manufacturer. The template DNA was generated by PCR amplifying a 363 bp fragment of the *Trichoderma reesei* Cel6A cellobiohydrolase II coding region, representing the entire double stranded RNA sequence from pTr0749 using primers 998305 (sense) and 998306 (antisense) shown below. The sense primer was engineered to have an Xba I site at the 5'-end and a Hind III site at the 5'-end of the antisense primer.

Primer 998305 (Sense):

```
Primer 998305 (sense):
5'-CTAGTCTAGAGTCGCAAAGGTTCCC-3'        (SEQ ID NO: 31)
```

Primer 998306 (Antisense):

```
Primer 998306 (antisense):
5'-GGGGGAAGCTTTGACTGAGCATT-3'         (SEQ ID NO: 32)
```

Figure 8:
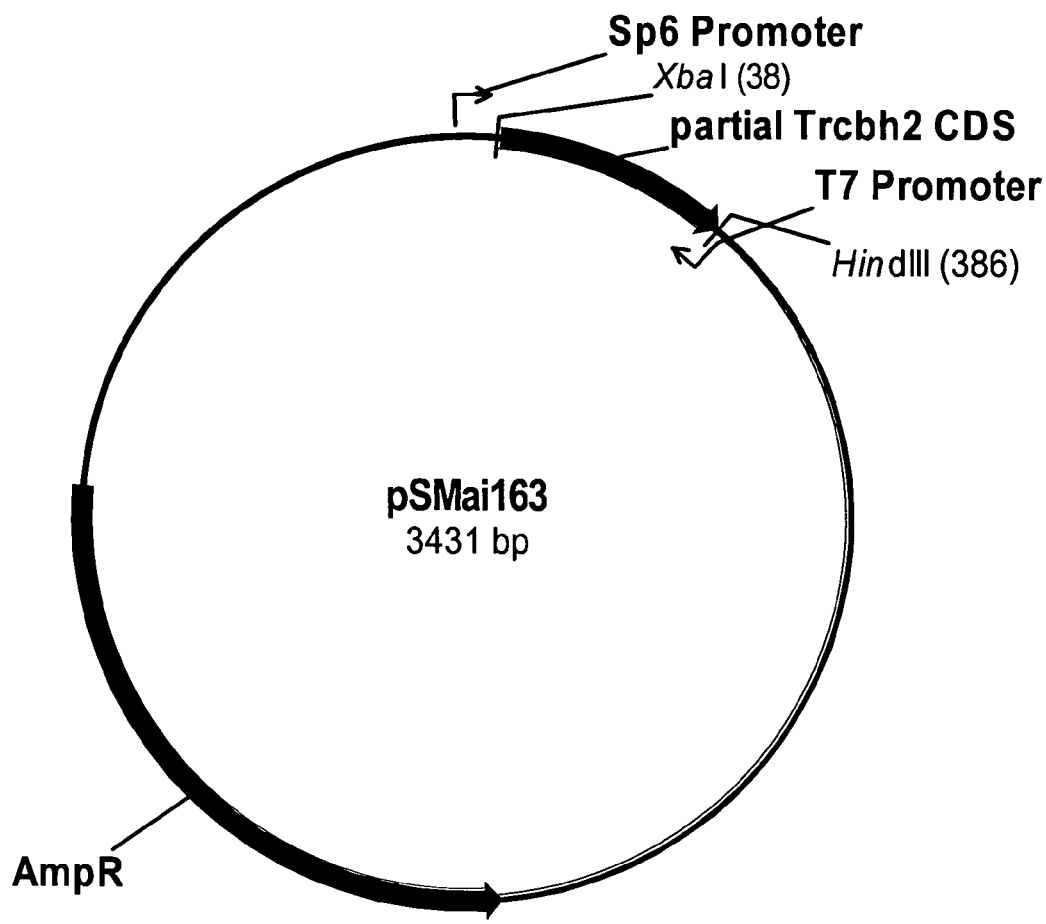
FIG. 8 shows a restriction map of pSMai163.

The amplification reactions (50 µl) were composed of 1× ThermoPol Reaction Buffer, 0.3 mM dNTPs, 10 ng pTr0749, 0.3 µM primer 998305, 0.3 µM primer 998306, and 2.5 units of Taq polymerase. The reactions were incubated in an Eppendorf Mastercycler 5333 programmed as follows: 30 cycles each for 30 seconds at 94° C., 30 seconds at 56° C., and 30 seconds at 72° C. (15 minute final extension). The reaction products were isolated on a 1.0% agarose gel using TAE buffer where a 383 bp product band was excised from the gel and purified using a QIAquick Gel Extraction Kit according to the manufacturer's instructions. The resulting *Trichoderma reesei* Cel6A cellobiohydrolase II PCR fragment was digested with Xba I and Hind III and ligated into Xba I and Hind III digested pSPT19 vector (Roche Molecular Biochemicals, Indianapolis, Ind., USA), using T4 DNA ligase according to manufacturer's protocol, to generate pSMai163 (FIG. 8).

Hybridization was performed in DIG Easy Hyb buffer (Roche Molecular Biochemicals, Indianapolis, Ind., USA) at 42° C. for 15-17 hours. The membrane was then washed under high stringency conditions in 2×SSC plus 0.1% SDS for 5 minutes at room temperature followed by two washes in 0.1×SSC plus 0.1% SDS for 15 minutes each at 42° C. The probe-target hybrids were detected by chemiluminescent assay (Roche Molecular Biochemicals, Indianapolis, Ind.), following the manufacturer's instructions.

Figure 9:
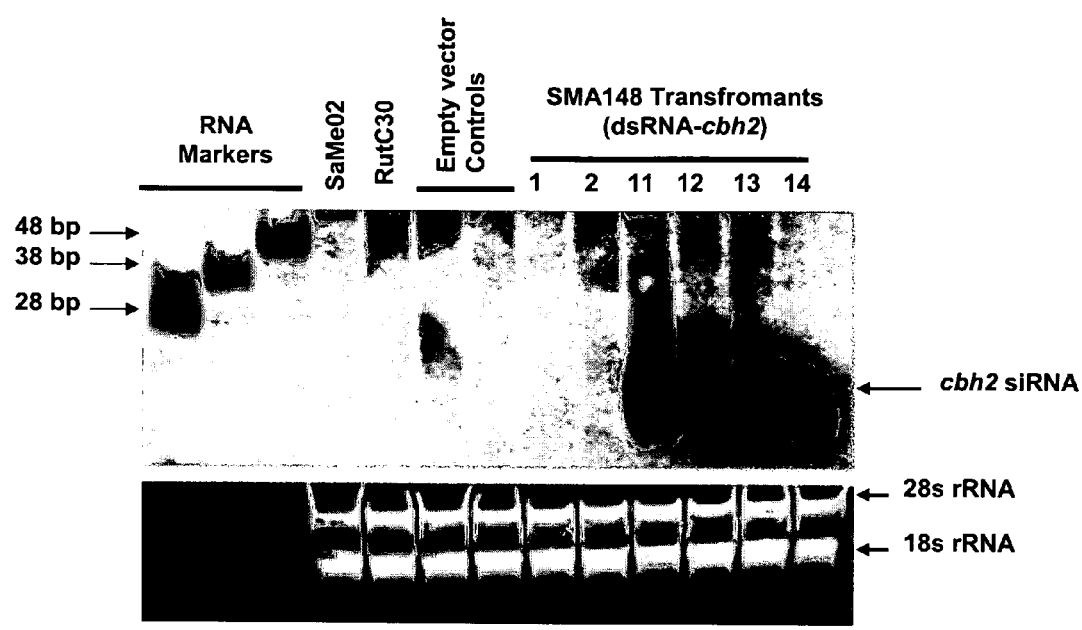
FIG. 9 shows detection of small interfering *Trichoderma reesei* Cel6A cellobiohydrolase II RNA by Northern analysis. Total RNAs (25 µg) were electrophoresed onto a 15% polyacrylamide-7M urea gel, transferred to a nylon membrane and probed with a DIG-labeled *Trichoderma reesei* Cel6A cellobiohydrolase II RNA probe. *Trichoderma reesei* SaMe02 was a positive control strain where the *Trichoderma reesei* Cel6A cellobiohydrolase II gene was knocked-out by homologous recombination. *Trichoderma reesei* RutC30 was the host strain. The ethidium bromide stained gel, which showed the control 28s-rRNA and 18s-rRNA, indicated equal loading.

Northern blot analysis revealed that transformants expressing the *Trichoderma reesei* Cel6A cellobiohydrolase II inverted repeat fragments produced small interfering *Trichoderma reesei* Cel6A cellobiohydrolase II RNA of approximately 21 bp (FIG. 9). The same RNAs were not detected in transformants containing vector controls, i.e., *Trichoderma reesei* RutC30 or *Trichoderma reesei* SaMe02 (where the *Trichoderma reesei* Cel6A cellobiohydrolase II gene was knocked-out by homologous recombination). These results indicated that double stranded RNA-mediated regulation of *Trichoderma reesei* Cel6A cellobiohydrolase II gene expression in *Trichoderma reesei* involved the production of small RNAs of the size range expected for a mechanism involved in RNA interference.

Example 20

Figure 10:
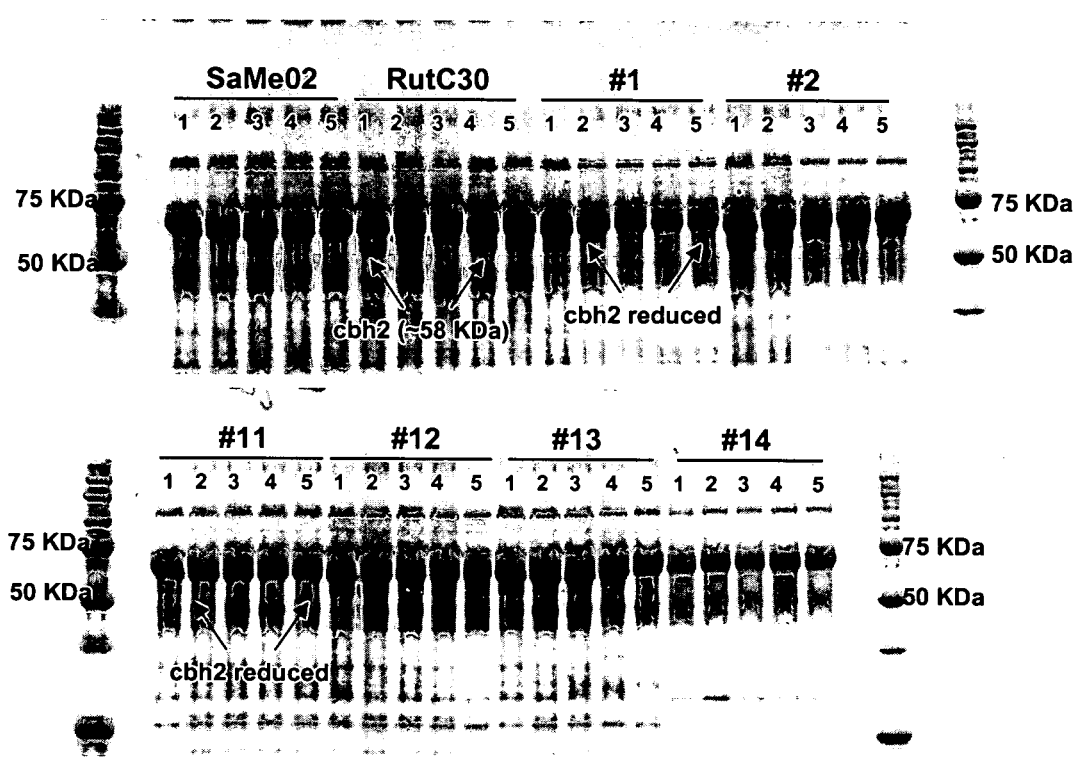
FIG. 10 shows SDS-PAGE analysis of day 7 shake flask samples (#'s 1, 2, 11, 12, 13, and 14) of *Trichoderma reesei* RutC30 expressing the *Trichoderma reesei* Cel6A cellobiohydrolase II inverted repeat fragments. *Trichoderma reesei* SaMe02 was a positive control strain where the *Trichoderma reesei* Cel6A cellobiohydrolase II gene was knocked-out by homologous recombination. *Trichoderma reesei* RutC30 was the host strain. At 7-days post-inoculation, 500 µl of mycelia were used as an inoculum for shake flasks containing fresh in cellulase-inducing medium. This passaging of mycelia was performed for a total of five rounds.

Long Term Stability of the *Trichoderma reesei* Silenced Cel6A Cellobiohydrolase II Transformants To evaluate the stability of the silenced *Trichoderma reesei* Cel6A cellobiohydrolase II transformants, spores from six transformants (#1, 2, 11, 12, 13 and 14) exhibiting varying degrees of *Trichoderma reesei* Cel6A cellobiohydrolase II protein reduction, the host strain *Trichoderma reesei* RutC30, and a positive control strain *Trichoderma reesei* SaMe02 were grown under inducing conditions in cellulase-inducing medium at pH 6.0. At 7-days post-inoculation, 500 µl of mycelia were used as an inoculum for shake flasks containing fresh in cellulase-inducing medium. This passaging of mycelia was performed for a total of five rounds. Supernatant from each round of passaging for each transformant was collected and analyzed by SDS-PAGE as described in Example 12. As FIG. 10 shows, silencing was maintained throughout the five generations for all the transformants.

Example 21

Construction of pAILo2 Expression Vector

Figure 11:
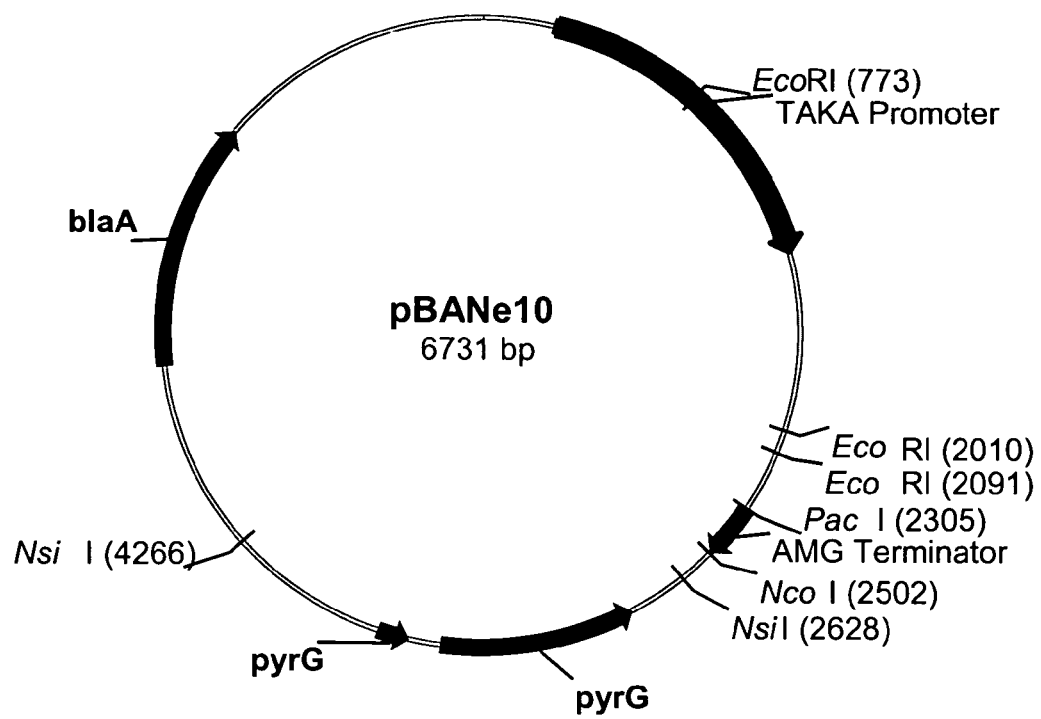
FIG. 11 shows a restriction map of pBANe10.
Figure 12:
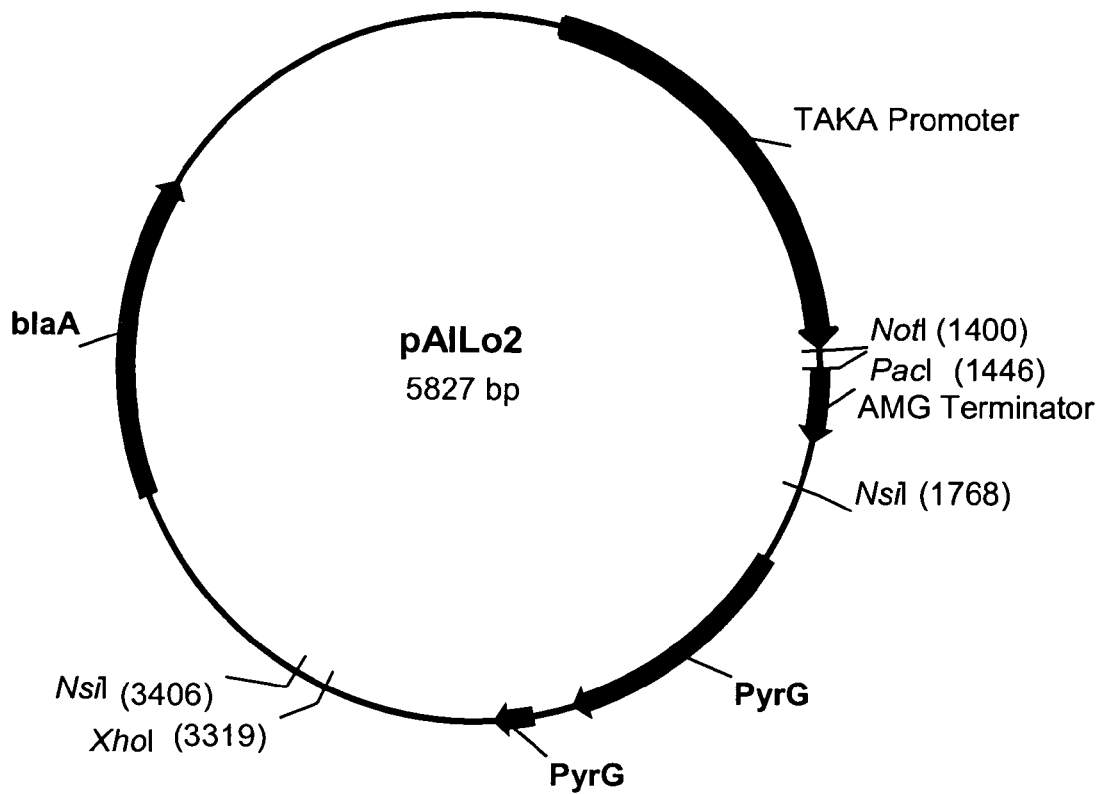
FIG. 12 shows a restriction map of pAILo2.

The amdS gene of pAILo1 (Example 1) was swapped with the *Aspergillus nidulans* pyrG gene. Plasmid pBANe10 (FIG. 11) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAILo1 and pBANe10 were digested with the Nsi I and the products purified by agarose gel electrophoresis. The Nsi I fragment from pBANe10 containing the pyrG gene was ligated to the backbone of pAILo1 to replace the original Nsi I DNA fragment containing the amdS gene. Recombinant clones were analyzed by restriction digest to determine that they had the correct insert and also its orientation. A clone with the pyrG gene transcribed in the counterclockwise direction was selected. The new plasmid was designated pAILo2 (FIG. 12).

Example 22

Construction of pHB506

Two fragments, one composed of a 184 bp Inverted Repeat (IR) and the other composed of 290 bp containing the 184 bp sequence in the opposite orientation along with a 106 linker region designated Inverted Repeat-Linker (IR-L) were PCR amplified from exon 4 of an amyloglucosidase gene of *Aspergillus niger* JaL303-10 (*Aspergillus niger* NN049453 is a strain originally generated from *Aspergillus niger* C40, which was isolated from the soil in 1960's, of which amyloglucosidase activity has been enhanced by mutagenesis. The *Aspergillus niger* strain JaL303 was constructed by site-directed gene disruption to cause the interruption of the resident tripeptidyl aminopeptidase gene in *Aspergillus niger* NN049453. *Aspergillus niger* JaL303-10 is a pyrG minus mutant strain of JaL303 spontaneously isolated on agar containing 5-FOA.)

Using 200 ng of genomic DNA as template, the primers below were employed. The sense primer was engineered to have an Nco I site at the 5'-end and a Not I site at the 5'-end of the antisense primer.

Primer 997491 (Sense):

```
                                          (SEQ ID NO: 33)
Primer 997491 (sense):
Sense 5'-GGGGCCATGGTCCTGGTGTGATTCTCAGGCACCCGAAATTC
                                                    TCTGC-3'
```

Primer 997492 (Sense):

```
                                          (SEQ ID NO: 34)
Primer 997492 (antisense):
5'-GGGGGCGGCCGCAGCAGGGCTGGAAGGTGGAGTCGTCGCATG-3'
```

Four hundred µl of *Aspergillus niger* JaL303-10 spores were grown in 50 ml of YP medium in a baffled shake flask at 34° C. and 150 rpm for 18 hours. Genomic DNA was then extracted from the mycelia using a DNeasy Plant Mini Kit (QIAGEN Inc., Valencia, Calif.) according to manufacturer's instructions.

The amplification reactions (50 µl) were composed of 1×Pfx Reaction Buffer (Invitrogen, Carlsbad, Calif.), 100 ng of *Aspergillus niger* JaL303-10 genomic DNA, 0.3 µM sense primer, 0.3 µM antisense primer, and 2.5 units of Pfx polymerase (Invitrogen, Carlsbad, Calif.). The reactions were incubated in an Eppendorf Thermocycler 5333 programmed as follows: 30 cycles each for 30 seconds at 94° C., 30 seconds at 56° C., and 30 seconds at 72° C. (15 minute final extension). The reaction product was isolated on a 1.0% agarose gel using TAE buffer where a 184 bp product band was excised from the gel and purified using a QIAquick Gel Extraction Kit according to the manufacturer's instructions.

For amplification of the inverted repeat in the reverse orientation plus the linker sequence, the sense primer was engineered to have a Pac I site at the 5' end and a Not I site at the 5' end of the antisense primer.

Primer 997493 (Sense):

(SEQ ID NO: 35)
Primer 997493 (sense):
5'-GGGGTTAATTAATCCTGGTGTGATTCTCAGGCACCCGAAATTCT
C-3'

Primer 997494 (Sense):

(SEQ ID NO: 36)
Primer 997494 (antisense):
5'-GGGGGCGGCCGCTACCGACCCACCGCAACAGCCTCGCTGTCA-3'

The amplification reactions (50 µl) were performed as described above. The reaction product was isolated on a 1.0% agarose gel using TAE buffer where a 290 bp product band was excised from the gel and purified using a QIAquick Gel Extraction Kit according to the manufacturer's instructions.

The resulting PCR fragment of 290 bp was then inserted into pTOPO Blunt (Invitogen Carlsbad, Calif.) according to the manufacturer's instructions to produce pTOPO-IR-L.

Figure 13:
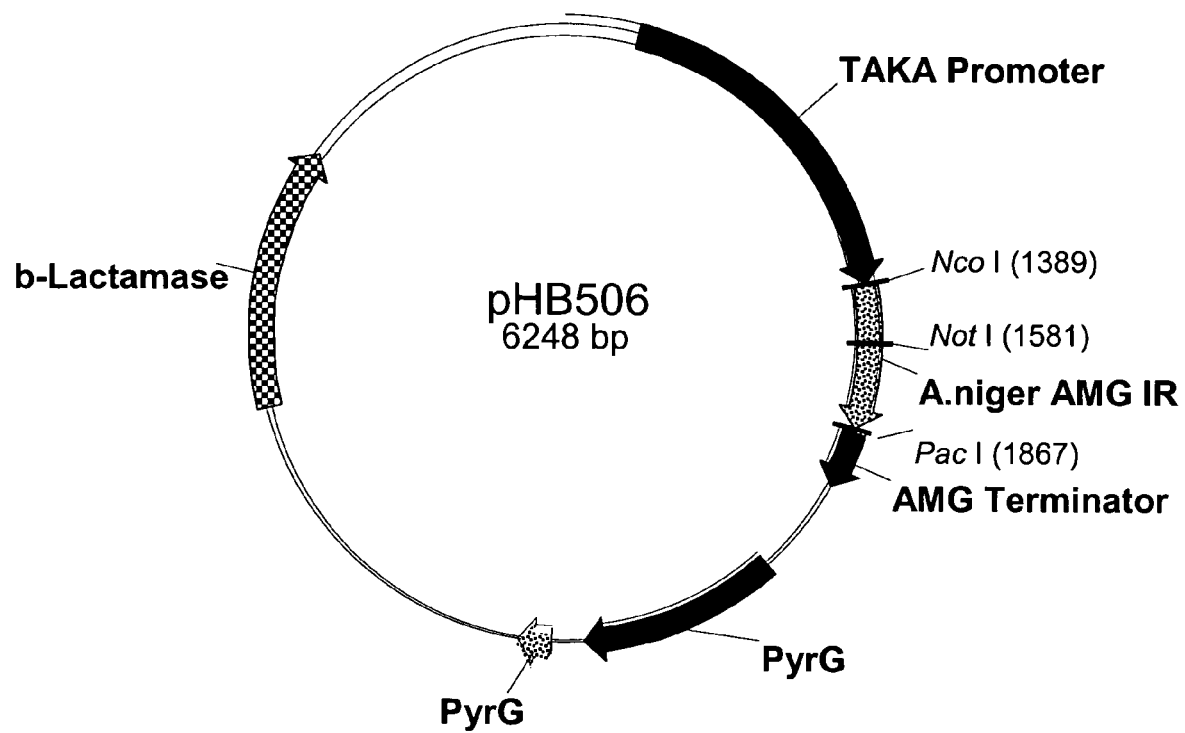
FIG. 13 shows a restriction map of pHB506.

Plasmid pTOPO-IR-L was digested with Pac I and Not I, purified using 1.0% agarose gel electrophoresis and a QIAquick Gel Extraction Kit as described above, and inserted into the corresponding restriction sites of pAILo2 resulting in pAILo2IR-L. The 184 bp fragment was isolated after digestion of pTOPO-IR and inserted into Nco I/Not I digested pAILo2IR-L resulting in pHB506 (FIG. 13).

Example 23

Transformation of pHB506 into *Aspergillus niger* JaL303-10

Protoplasts of *Aspergillus niger* JaL303-10 were prepared using the modified protocol described in Example 11. The protoplasts were counted using a haemacytometer and resuspended to a final concentration of $1 \times 10^7$ protoplasts per ml of STC. Excess protoplasts were stored in a Cryo 1° C. Freezing Container (Nalgene, Rochester, N.Y.) at −80° C.

Transformation of the *Aspergillus niger* JaL303-10 protoplasts with pHB506 and pAILo2 (as a control) was performed as described in Example 11 with the following modifications. Approximately 7 µg of pHB506 or pAILo2 was added to 100 µl of the protoplast solution and mixed gently. PEG buffer (250 µl) was added, mixed, and incubated at room temperature for 30 minutes. STC (3 ml) was then added, mixed, and plated onto Minimal Medium plates. The plates were incubated at 34° C. for 5-7 days.

Approximately 70 transformants were obtained. Spores from the 70 transformants were streaked onto Minimal Medium plates and incubated at 34° C. for 6 days to obtain primary transformants.

The primary transformants, along with *Aspergillus niger* JaL303-10 transformed with pAILo2, were then submitted to a plate assay to measure glucoamylase activity using maltose as a substrate. Release of glucose was determined using a coupled glucose oxidase/horseradish peroxidase/ABTS (2,2'-azino-bis(3-ethylbenzothiazoline-6-sulfonic acid) assay which produces a violet color. All reagents were from Sigma Chemical Company, St. Louis, Mo. M400 medium containing 20% Noble agar was autoclaved, cooled to 50° C. at which time 50 ml of 20% maltose (sterile filtered), 3 ml of 2.65% w/v ABTS stock solution, and 2 ml of HRP stock solution (100 U of horseradish peroxidase per ml of 0.1 M sodium acetate pH 5.0) were added. Two ml of the medium were added to each well of a 12 well cell culture plate. The plates were either wrapped in foil or placed in a light-proof box and stored at 4° C. Inoculating loops were used to transfer spores of each primary transformant to the assay wells. The plates were wrapped in foil and incubated at 34° C. for 1-2 days. Glucose oxidase solution (1.5 U of glucose oxidase per ml of 0.1 M sodium acetate pH 5.0) was then sprayed onto the plates which were then wrapped in foil and incubated at 34° C. for 1-2 hours. Glucoamylase activity was determined by the oxidation of ABTS indicated by color intensity of the colonial halo.

After incubation, the results showed that the color intensity of each transformant varied in its shade of violet with that of *Aspergillus niger* JaL303-10 transformed with pAILo2 being the darkest and several of the transformants displaying little or no glucoamylase activity.

Example 24

Shake Flask Analysis of Transformants

Based on the colorimetric screen described in Example 23, spores from eight transformant colonies were streaked onto Minimal Medium plates. Four transformants displaying little or no glucoamylase activity and 4 randomly chosen transformants producing variable amyloglucosidase activity based on colorometric plate assay were selected for growth in shake flasks. The above transformants along with *Aspergillus niger* HowB112 having glucoamylase and neutral amylase deletions, prepared as described in WO 04/090155, *Aspergillus niger* JaL303-10, and *Aspergillus niger* JaL303-10 transformed with pAILo2 were grown in shake flasks containing M400 medium.

Shake flasks (125 ml, baffled) containing 25 ml of M400 medium were inoculated with spores of each *Aspergillus niger* transformant that grew on Minimal Medium plates and the controls described above and incubated at 34° C. and 200 rpm for 3 days. Culture broth samples were removed 3 days post-inoculation and centrifuged at 15,700×g for 5 minutes in a micro-centrifuge. The supernatants were transferred to new tubes and stored at 4° C. until SDS-PAGE analysis.

SDS-PAGE was carried out using Criterion™ Tris-HCl gels with The Criterion™ Cell. Five µl of day 3 samples were suspended in 2× concentration of Laemmli Sample Buffer (Bio-Rad Laboratories, Hercules, Calif.) and boiled for 3 minutes in the presence of 5% β-mercaptoethanol. Samples were loaded onto a SDS-PAGE gel and subjected to electrophoresis in 1×Tris/Glycine/SDS running buffer (Bio-Rad Laboratories, Hercules, Calif.). The resulting gel was stained with Bio-Safe™ Coomassie Stain (Bio-Rad Laboratories, Hercules, Calif.).

Figure 14:
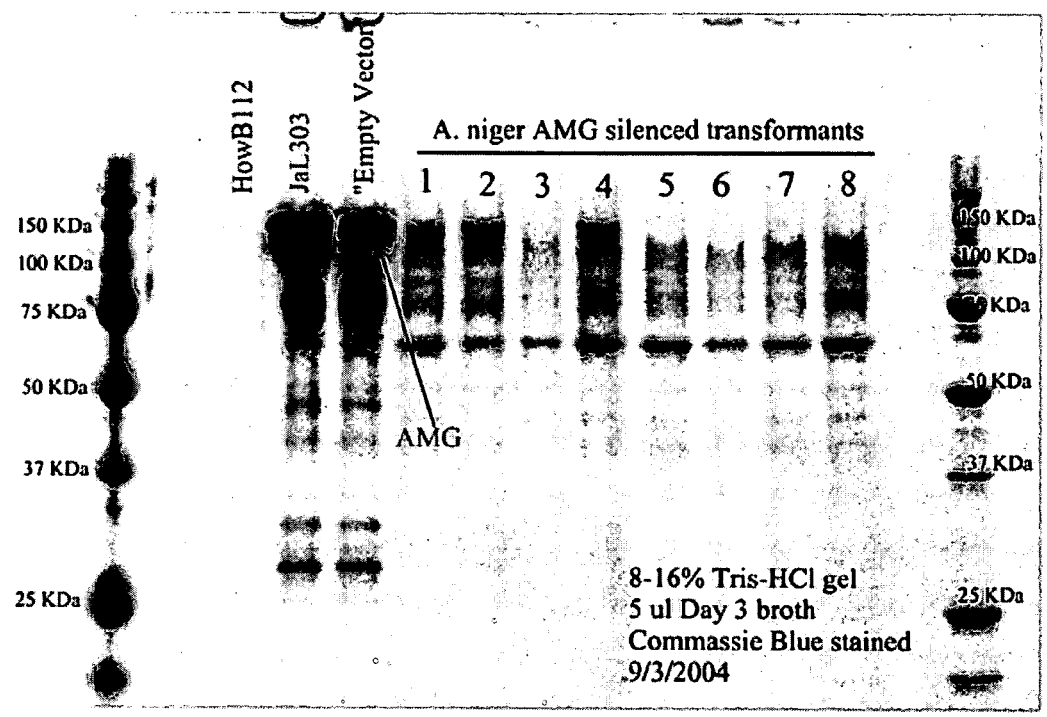
FIG. 14 shows SDS-PAGE analysis of day 7 shake flask samples of selected *Aspergillus niger* transformants containing pHB506 (transformants 1-8), a glucoamylase gene deleted strain *Aspergillus niger* HowB112, *Aspergillus niger* JaL303-10, and *Aspergillus niger* JaL303-10 transformed with pAILo2 (empty vector). Transformants 1-4 produced viable amounts of glucoamylase whereas transformants 5-8 produced no detectable glucoamylase.

The SDS-PAGE results (FIG. 14) showed the presence of two proteins, a predominant band at approximately 125 kDa, thought to be a precursor and a more diffuse band, or bands, at 75 kDa known to be the processed enzyme. Both of these protein bands were present in *Aspergillus niger* JaL303-10 transformed with pAILo2. In contrast, the glucoamylase gene deleted strain *Aspergillus niger* HowB112 lacked either band. The selected transformants produced lesser amounts of these two proteins. Transformants 1-4 representing randomly picked strains produced viable amounts of glucoamylase whereas transformants 5-8, lacking glucoamylase as measured in the plate screen, produced no detectable glucoamylase. These results suggested that expression of the *Aspergillus niger* glucoamylase was suppressed as a result of RNAi.

Example 25

Construction of pHUda512 Expression Vector

Expression vector pHUda512 was constructed for transcription of double stranded-RNA derived from the amyloglucosidase gene of *Aspergillus niger* NN049735. The production of the cDNA sequence of the *Aspergillus niger* amyloglucosidase gene and the cDNA clone of the *Aspergillus niger* amyloglucosidase gene are described in WO 00/004136. A PCR reaction with the cDNA clone of the *Aspergillus niger* amyloglucosidase gene as template was performed with an Expand™ PCR system (Roche Diagnostics, Japan) using primers HU704 to introduce Bgl II, Kpn I, and Xho I sites and primer HU705 to introduce a BamH I site, as shown below.

```
                                        (SEQ ID NO: 37)
HU704:
5'-TTTAGATCTCTCGAGGTACCAAATGTGATTTCCAAGCGCGCG-3'

(SEQ ID NO: 38)
HU705:
5'-TTTGGATCCAAGAGATCGACGAGGGTCTTG-3'
```

The amplification reactions (50 µl) were composed of 1 ng of template DNA per µl, 250 mM dNTP each, 250 nM primer HU704, 250 nM primer HU705, 0.1 U of Taq polymerase per µl in 1× buffer (Roche Diagnostics, Japan). The reactions were incubated in a DNA Engine PTC-200 (MJ-Research, Japan) programmed as follows: 1 cycle at 94° C. for 2 minutes; 30 cycles each at 92° C. for 1 minute, 55° C. for 1 minute, and 1 cycle at 72° C. for 1 minute; 1 cycle at 72° C. for 10 minutes; and a hold at 4° C.

The reaction products were isolated on a 1.0% agarose gel using TAE buffer where a 213 bp product band was excised from the gel and purified using a QIAquick™ Gel Extraction Kit (QIAGEN Inc., Valencia, Calif.) according to the manufacturer's instructions.

The 213 bp amplified DNA fragment was digested with Bgl II and BamH I and ligated into pMT2188 (WO 03/089648) digested with BamH I. The ligation mixture was transformed into *E. coli* DB6507 (ATCC 35673) using the *Saccharomyces cerevisiae* URA 3 gene as selective marker to create the expression plasmid pHUda508. The amplified plasmid was recovered using a QIAprep® Spin Miniprep kit (QIAGEN Inc., Valencia, Calif.) according to the manufacturer's instructions.

Plasmid pMT2188 comprised an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglucosidase terminator (AMG terminator), the selective marker amdS from *Aspergillus nidulans* enabling growth on acetamide as sole nitrogen source, and the URA3 marker from *Saccharomyces cerevisiae* enabling growth of the pyrF defective *Escherichia coli* strain DB6507.

A separate PCR was performed with the cDNA clone of the *Aspergillus niger* amyloglucosidase gene as template with an Expand™ PCR system using primer HU704 to introduce Bgl II, Kpn I and Xho I sites and primer HU706 to introduce a BamH I site, as shown below.

```
                                        (SEQ ID NO: 39)
HU704:
5'-TTTAGATCTCTCGAGGTACCAAATGTGATTTCCAAGCGCGCG-3'

(SEQ ID NO: 40)
HU706:
5'-TTTGGATCCTAGGCAGTCTCATCGACATTG-3'
```

The amplification reactions (50 µl) were composed of 1 ng of template DNA per µl, 250 mM dNTPs each, 250 nM primer HU704, 250 nM primer HU706, 0.1 U of Taq polymerase per µl in 1× buffer (Roche Diagnostics, Japan). The reactions were incubated in a DNA Engine PTC-200 programmed as follows: 1 cycle at 94° C. for 2 minutes; 30 cycles each at 92° C. for 1 minute, 55° C. for 1 minute, and 1 cycle at 72° C. for 1 minute; 1 cycle at 72° C. for 10 minutes; and a hold at 4° C.

The reaction products were isolated on a 1.0% agarose gel using TAE buffer where a 366 bp product band was excised from the gel and purified using a QIAquick™ Gel Extraction Kit (QIAGEN Inc., Valencia, Calif.) according to the manufacturer's instructions.

Figure 15:
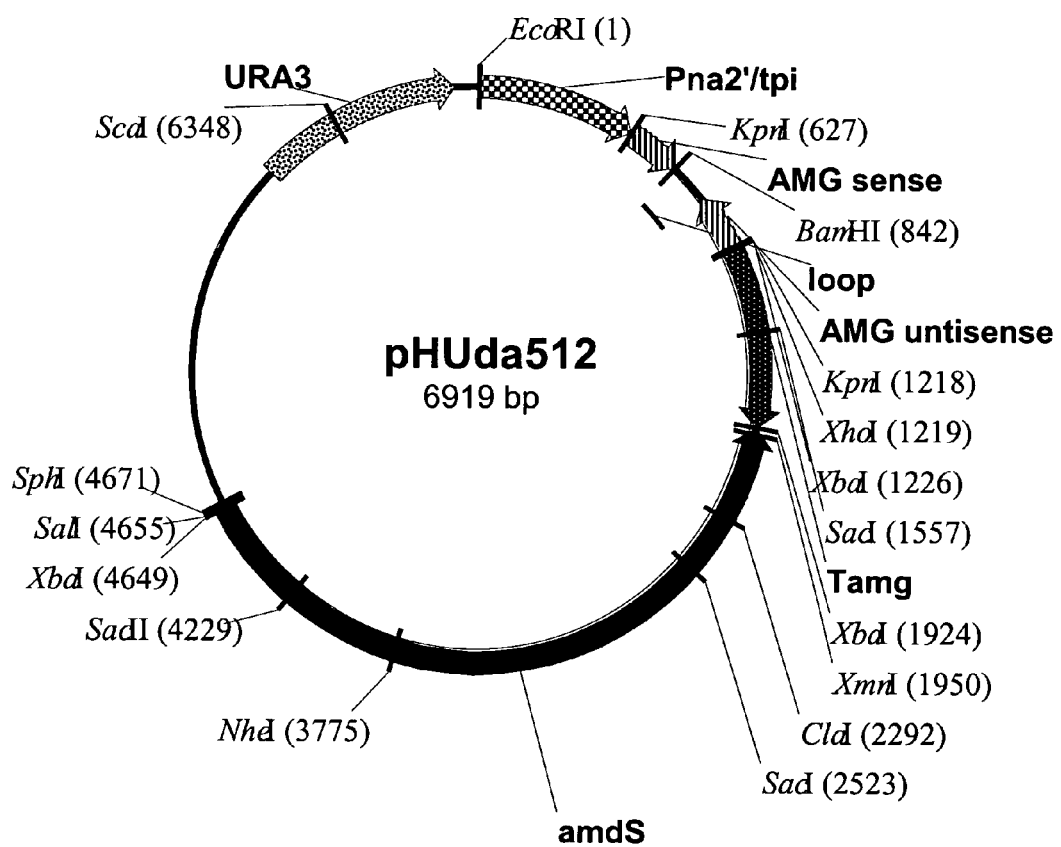
FIG. 15 shows a restriction map of pHUda512.

The 366 bp amplified DNA fragment was digested with Xho I and BamH I and ligated into pHUda508 digested with BamH I and Xho I. The ligation mixture was transformed into *E. coli* DB6507 (ATCC 35673) to create the expression plasmid pHUda512 (FIG. 15) containing a 213 bp inverted repeat derived from the *Aspergillus niger* amyloglucosidase coding region. The amplified plasmid was recovered using a QIAprep® Spin Miniprep Kit according to the manufacturer's instructions.

Example 26

Expression of Double Strand-RNA Derived from an *Aspergillus niger* Amyloglucosidase Gene

*Aspergillus niger* strain NN049735 produces both *Aspergillus niger* amyloglucosidase and hybrid enzyme between *Aspergillus niger* acid stable alpha-amylase and a carbohydrate-binding module derived from *Aspergillus kawachii* acid stable alpha-amylase.

*Aspergillus niger* NN049735 was cultivated in 100 ml of non-selective YPG medium at 32° C. for 16 hours on a rotary shaker at 120 rpm. Cells were collected by filtering, washed with 0.6 M KCl, and resuspended in 20 ml of 0.6 M KCl containing beta-glucanase (GLUCANEX™, Novozymes A/S, Bagsværd, Denmark) at a final concentration of 600 µl per ml. The suspension was incubated at 32° C. and 80 rpm until protoplasts were formed, and then washed twice with STC buffer. The protoplasts were counted with a haemacytometer and resuspended and adjusted in an 8:2:0.1 solution of STC:STPC:DMSO to a final concentration of $2.5 \times 10^7$ protoplasts/ml. Approximately 3 µg of pHUda512 was added to 100 µl of the protoplast suspension, mixed gently, and incubated on ice for 20 minutes. One ml of SPTC was added and the protoplast suspension was incubated for 30 minutes at 37° C. After the addition of 10 ml of 50° C. COVE top agarose, the reaction was poured onto COVE agar plates and the plates were incubated at 32° C. After 5 days transformants were selected from the COVE medium.

Eight randomly selected transformants were inoculated into 100 ml of MLC medium and cultivated at 30° C. for 2 days. Ten ml of MLC medium was inoculated into 100 ml of MU-1 medium and cultivated at 30° C. for 7 days. Supernatants were obtained by centrifugation at 3,000×g for 10 minutes.

Glucoamylase activity in the supernatant samples was determined as an increase in NADH production by glucose dehydrogenase and mutarotase reaction with generating glucose and measured the absorbance at 340 nm. Six µl of enzyme samples dissolved in 100 mM sodium acetate pH 4.3 buffer was mixed with 31 µl of 23.2 mM of maltose in 100 mM sodium acetate pH 4.3 buffer and incubated at 37° C. for 5 minutes. Then, 313 µl of color reagent (430 U of glucose dehydrogenase per liter, 9 U mutarotase per liter, 0.21 mM NAD, and 0.15 M NaCl in 0.12 M phosphate pH 7.6 buffer) was added to the reaction mixture and incubated at 37° C. for 5 minutes. Activity was measured at 340 nm on a spectrophotometer. Six µl of distilled water was used in place of the enzyme samples as controls.

Glucoamylase activity was measured in AmyloGlucosidase Units (AGU), which was determined relative to an enzyme standard obtained from Novozymes A/S, Bagsværd, Denmark. One AGU is defined as the amount of enzyme that hydrolyzes 1 micromole of maltose per minute at 37° C. in 23.2 mM maltose in 0.1 M sodium acetate pH 4.3 buffer.

Acid stable alpha-amylase activity was determined in the supernatant samples as a decrease of blue color of starch-iodine complex measured at 590 nm. Twenty-five µl of enzyme samples dissolved in 51.4 mM calcium chloride in 2 mM citrate pH 2.5 buffer were mixed with 135 µl of 0.6 g of soluble starch (Merck 1253, Germany) and 12 g of sodium acetate per liter of 100 mM sodium citrate pH 2.5 buffer, and incubated at 37° C. for 325 sec. After 325 sec, 90 µl of iodine solution (1.2 g of potassium iodide and 0.12 g of iodine per liter) was added to the reaction mixture and incubated at 37° C. for 25 seconds. Activity was measured at 590 nm on a spectrophotometer. Twenty-five µl of distilled water was used in place of the enzyme samples as controls.

Acid stable alpha-amylase activity was measured in AFAU (Acid Fungal Alpha-amylase Units), which was determined relative to an enzyme standard obtained from Novozymes A/S, Bagsværd, Denmark. One FAU is defined as the amount of enzyme which degrades 5.260 mg starch dry matter per hour under the conditions described above.

Table 2 shows amyloglucosidase activity and acid stable alpha-amylase activity of the selected transformants, relative to the activity of the host strain, *Aspergillus niger* NN049735, which was normalized to 1.0. The results demonstrated the decrease of amyloglucosidase activity and increase of acid stable alpha-amylase activity simultaneously compared to the host strain *Aspergillus niger* NN049735.

TABLE 2

Shake flask results of the selected transformants

| Strains | A. niger AMG (AGU/ml) Relative activities | Acid stable alpha-amylase (AFAU/ml) Relative activities |
|---|---|---|
| # 5 | 0.01 | 1.43 |
| # 19 | 0.03 | 1.57 |
| # 20 | 0.01 | 1.23 |
| # 50 | 0.02 | 1.37 |
| # 64 | 0.05 | 1.34 |
| # 65 | 0.01 | 0.97 |
| # 77 | 0.04 | 1.46 |
| # 97 | 0.01 | 1.23 |
| NN049735 | 1.0 | 1.00 |

Figure 16:
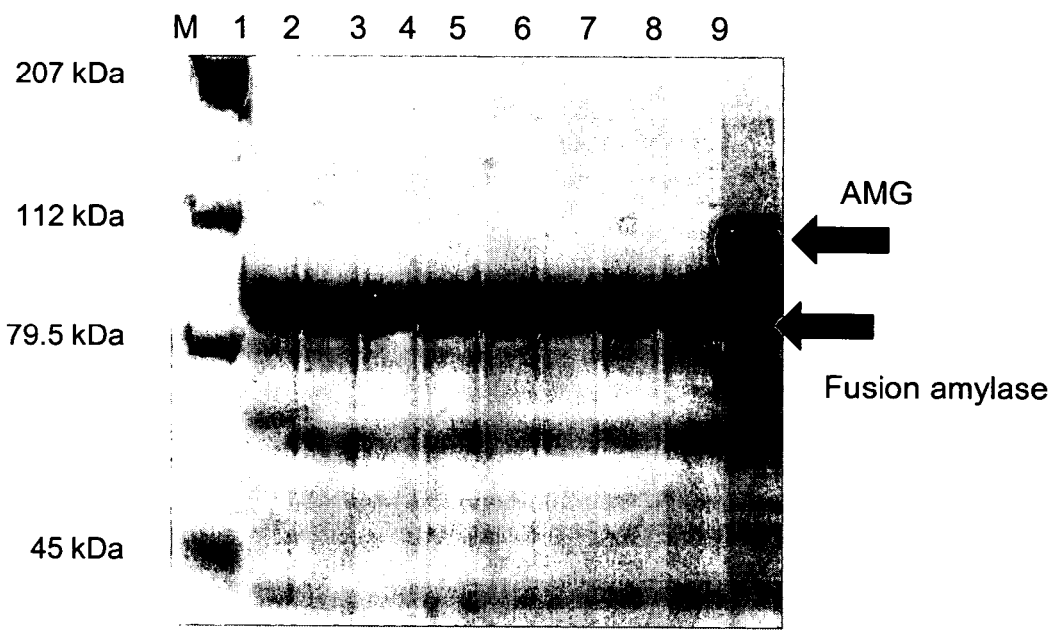
FIG. 16 shows SDS-PAGE analysis of day 7 shake flask samples of selected *Aspergillus niger* transformants containing pHUda512 (lane 1-8) and *Aspergillus niger* NN049735 (lane 9).

SDS-PAGE analysis was carried out using e-PAGEL gels E-T 7.5 L (ATTO Corporation, Japan). Ten µl of day 7 samples were suspended in 2× concentration of Sample Buffer (1% SDS, 1% β-mercaptoethanol, 1 mg/ml bromophenolblue, 10% glycerol, and 50 mM Tris-HCl pH 6.8), and boiled for 5 minutes. The samples were loaded onto an e-PAGEL gel and subjected to electrophoresis in 1×Tris/Glycine/SDS running buffer (25 mM Tris-HCl, 0.1% SDS, 192 mM glycine) at 20 mA for 90 minutes. The resulting gel (FIG. 16) was stained with stain solution (1 g/L Coomassie brilliant blue, 10% acetic acid, 30% methanol) for 30 minutes and then destained with destaining solution (10% acetic acid, 30% methanol) until the bands were visible.

Dominant bands at approximately 100 kDa and 80 kDa corresponding to *Aspergillus niger* amyloglucosidase and fusion enzyme between *Aspergillus niger* acid stable alpha-amylase fusion protein, respectively, were present in *Aspergillus niger* NN049735. In contrast, the selected transformants produced lower amounts of the *Aspergillus niger* amyloglucosidase band and higher amounts of the *Aspergillus niger* acid stable alpha-amylase fusion protein band.

Example 27

Screening for Morphological Mutants

The "e" pools and "b" pools described in WO 98/11203 (Example 5) were screened for colonies having altered morphology by plating on CM-1 agar and incubating at 34° C. for 4 days. Colonies having altered plate morphology within the pool were transferred to a fresh CM-1 agar plate and incubated 5 days at 34° C. for single colony isolation. Each morphological mutant on a plate was transferred from a single colony to the center of a CM-1 plate and a PDA plate, and incubated 6-8 days at 34° C. before the morphology was evaluated, i.e., the diameter and the appearance. A total of 218 morphological mutants was transferred to COVE2 plates and incubated at 34° C. for 1-2 weeks to generate spores. A mutant was identified which produced white spores and designated *Aspergillus oryzae* P2-5.1.

Example 28

Rescue and Characterization of Plasmid DNA and Flanking DNA from Morphological Mutant *Aspergillus oryzae* P2-5.1

The plasmid DNA and genomic flanking loci were isolated from mutant *Aspergillus oryzae* P2-5.1 using the procedure described in WO 98/11203 (Example 9) except for the restriction endonuclease used. An *E. coli* HB101 transformant containing a Bgl II rescued locus from mutant *Aspergillus oryzae* P2-5.1 was isolated.

The *Aspergillus oryzae* P2-5.1 rescued locus containing 535 and 750 bp regions on either side of the integration event was sequenced with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38: 47-60) using the M13 reverse (−48) and M13 forward (−20) primers (New England Biolabs, Beverly, Mass.) and primers unique to the DNA being sequenced. A 400 bp nucleic acid sequence (SEQ ID NO: 41) representing one flank of the rescued wA gene was chosen as the template of construction of the inverted repeat. The nucleic acid sequence suggested that the integration event occurred within an open reading frame for a homolog of the *Aspergillus fumigatus* wA gene (accession number Y17317). Nucleic acid homology of 74% was found and the deduced amino acid sequence (SEQ ID NO: 42) of the 400 bp fragment of the rescued locus shared 71% identity when compared to the deduced amino acid sequence of the *Aspergillus fumigatus* wA gene. The wA gene encodes a polyketide synthetase involved in the synthesis of the green pigment in wild-type spores. Mutants of this gene produce spores which lack pigment and appear white. Disruption of the wA gene in *Aspergillus nidulans* is known to change the spore color to white (Mayorga and Timberlak, 1992, *Mol. Gen. Genet.* 235: 205-212), which is the observed phenotype of *Aspergillus oryzae* P2-5.1.

Example 29

Construction of pDeMi01

To express dsRNA derived from the *Aspergillus oryzae* wA gene, all of one half of the inverted repeat of 175 base pairs from within the open reading frame of the wA gene was PCR amplified using a sense strand primer possessing a NotI restriction site and an antisense primer possessing a 5' Nhe I restriction site shown below.
Sense:

(SEQ ID NO: 43)
Sense: 5'-GGGGGCGGCCGCAGCACTTCGATTGCATTAGTCAAAA-3'

Antisense:

(SEQ ID NO: 44)
Antisense: 5'-GGGGGCTAGCAGAACGAACGCAGGTTTTAT-3'

The amplification reactions (50 µl) were composed of 1×Pfx Reaction Buffer, 100 ng of *Aspergillus oryzae* P2-5.1 genomic DNA (which was isolated using a DNeasy Plant Maxi Kit), 0.3 mM dNTPs, 0.3 µM sense primer, 0.3 µM antisense primer, and 2.5 units of Pfx polymerase. The reactions were incubated in an Eppendorf Thermocycler 5333 programmed as follows: 30 cycles each for 30 seconds at 94° C., 60 seconds at 58° C., and 1 minute at 72° C. (15 minute final extension). The reaction product was isolated on a 1.0% agarose gel using TAE buffer where a 175 bp product band was excised from the gel and purified using a QIAquick Gel Extraction Kit according to the manufacturer's instructions.

The other half of the inverted repeat including a 103 base pair spacer was amplified using the sense primer above and the antisense primer below having a Nhe I restriction site at the primer's 5' end.
Antisense:

(SEQ ID NO: 45)
Antisense: 5'-GGGGGCTAGCGGGTAGCCCGACGGCCACAAAGG-3'

The amplification reactions (50 µl) were performed in 1×Pfx Reaction Buffer, 0.3 mM dNTPs, 100 ng of *Aspergillus oryzae* P2-5.1 genomic DNA, 0.3 µM sense primer, 0.3 µM antisense primer, and 2.5 units of Pfx polymerase. The reactions were incubated in an Eppendorf Thermocycler 5333 programmed as follows: 30 cycles each for 30 seconds at 94° C., 45 seconds at 58° C., and 1 minute at 72° C. and a 15 minute final extension. The reaction product was isolated on a 1.0% agarose gel using TAE buffer where a 273 bp product was excised from the gel and purified using a QIAquick Gel Extraction Kit according to the manufacturer's instructions.

The two PCR products were digested with Nhe I. The 273 bp repeat plus spacer and the 175 bp repeat were mixed and ligated with T4 DNA ligase using conditions specified by the manufacturer. The ligation products were resolved on a 1.5% agarose gel. The 448 bp fragment corresponding to the inverted repeated was gel-isolated using a Qiaex II DNA Purification Kit (QIAGEN Inc., Valencia, Calif.) followed by Not I digestion. To drive the transcription of the inverted repeat, plasmid pBANe6 (U.S. Pat. No. 6,461,837) which contains the NA2-tpi promoter directly upstream of the Not I site was used. The plasmid was digested with Not I and dephosphorylated using shrimp alkaline phosphatase (Roche, Indianapolis, Ind.). De-phosphorylated linear plasmid and the 448 bp inverted repeat fragment were mixed and ligated using T4 DNA Ligase at 14° C. for 16 hours. Two µl of the ligation mix were used to transform competent *E. coli* SURE Cells (Stratagene, La Jolla, Calif.) according to the manufacturer's instructions.

Figure 17:
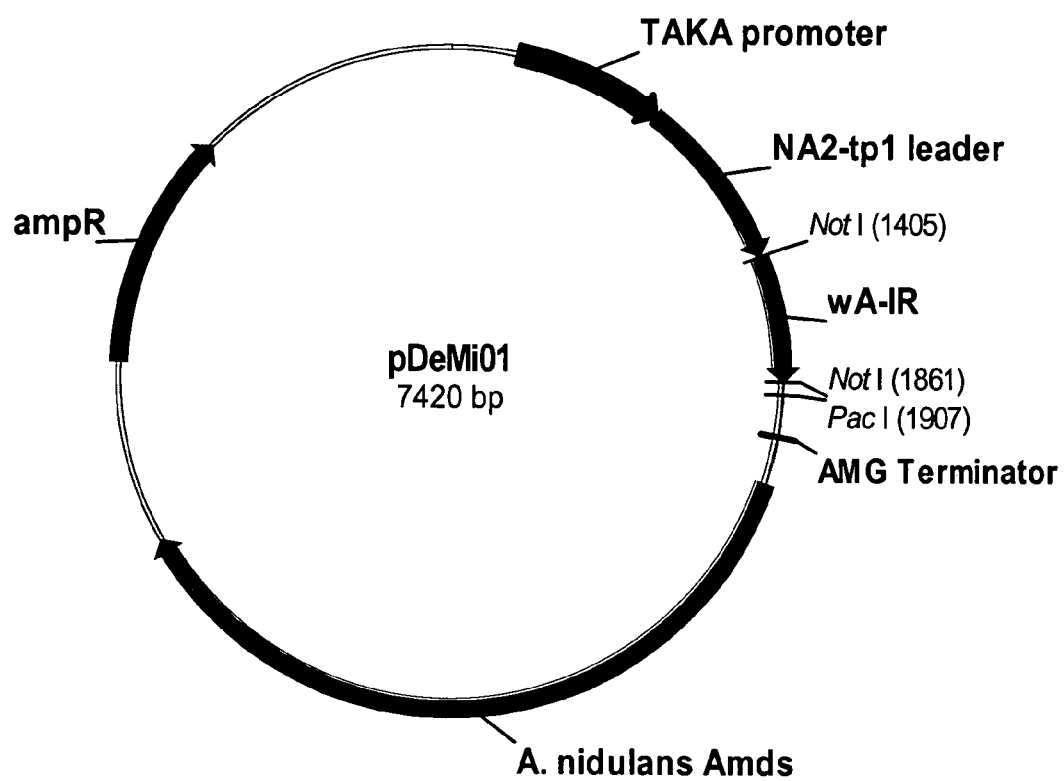
FIG. 17 shows a restriction map of pDeMi01.

Plasmid DNA from several transformants was recovered, digested with Not I, and resolved on a 1.5% agarose gel as above. Transformants containing a single fragment of approximately 500 bp was confirmed by DNA sequence analysis to consist of both the 175 bp repeat fragment the 175 bp fragment in the reverse orientation separated by the 103 bp spacer. One of the isolated plasmids was designated pDeMi0 (FIG. 17).

Example 24

Transformation of *Aspergillus oryzae* and Analysis of Transformants

Five µg of pDeMi01 or pBANe6 were used to transform protoplasts prepared from *Aspergillus oryzae* strain Jal250 (WO 98/11203) using growth on acetamide for selection. Growth on acetamide requires expression of the amdS gene present on pDeMi01. The transformation was performed as described in WO 98/11203 (Example 2). After incubation at 34° C. for 30 minutes, the protoplast/DNA mix was brought to 3 ml with STC and spread on COVE plates supplemented with 10 mM uridine. The plates where then incubated at 34° C. for 6 days.

Approximately 50 transformants were obtained using pDeMi01 or pBANe6. All the pBANe6 transformants possessed the dark green spores characteristic of wild-type *Aspergillus oryzae*. In contrast, the pDeMi01 transformants produced colors ranging from light yellow to dark green. The results suggested that the inverted repeat, when transcribed, formed a hairpin dsRNA inducing genes specific RNAi. Variation in spore color could be the result of differential transcription of the inverted repeat, possibly due to the chromosome integration site of the plasmid.

Eight primary transformants obtained using pDeMi01 and 1 transformant obtained with pBANe6 were streaked on COVE2 plates supplemented with 10 mM uridine. All colonies derived from pBANe6 were uniformly dark green. In contrast, the colonies obtained from the pDeMi01 transformants varied in spore color. Subsequent spore purifications yielded uniformity of spore color. Spores from plates transformed with pDeMi01 or pBANe8 were suspended in water, placed on slides and observed by light microscopy. Spores from the control pBANe8 strain remained green, whereas spores from pDeMi01 transformants appeared clear, the expected result of inactivation by RNA interference.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for reducing or eliminating the expression of a target gene encoding a biological substance in a filamentous fungal strain, comprising:
   (a) inserting into the genome of an *Aspergillus niger*, an *Aspergillus oryzae*, or a *Trichoderma reesei* strain a double-stranded transcribable nucleic acid construct comprising a first nucleotide sequence comprising a promoter operably linked to a first homologous transcribable region of the target gene encoding the biological substance and a second nucleotide sequence comprising a second homologous transcribable region of the target gene, wherein the first and second homologous regions are complementary to each other and the second homologous region is in reverse orientation relative to the first homologous region; and
   (b) inducing production of an interfering RNA encoded by the double-stranded transcribable nucleic acid construct by cultivating the *Aspergillus niger*, the *Aspergillus oryzae*, or the *Trichoderma reesei* strain under conditions conducive for production of the interfering RNA, wherein the interfering RNA interacts with RNA transcripts of the target gene to reduce or eliminate expression of the target gene encoding the biological substance.

2. The method of claim 1, wherein the first homologous region comprises at least 19 nucleotides of the target gene.

3. The method of claim 1, wherein the second homologous region comprises at least 19 nucleotides of the first homologous region, wherein the least 19 nucleotides are in reverse order relative to the corresponding region of the first homologous region.

4. The method of claim 1, wherein the first and second nucleotide sequences are separated by a third nucleotide sequence.

5. The method of claim 4, wherein the third nucleotide sequence comprises at least 5 nucleotides.

6. The method of claim 1, wherein expression of the target gene is eliminated.

7. The method of claim 1, wherein the interfering RNA interacts with RNA transcripts of one or more homologues of the target gene to reduce or eliminate expression of the one or more homologues of the target gene.

8. A filamentous fungal strain comprising a double-stranded transcribable nucleic acid construct comprising a first nucleotide sequence comprising a promoter operably linked to a first homologous transcribable region of a target gene encoding a biological substance and a second nucleotide sequence comprising a second homologous transcribable region of the target gene, wherein the first and second homologous regions are complementary to each other and the second homologous region is in reverse orientation relative to the first homologous region, wherein interfering RNA encoded by the double-stranded transcribable nucleic acid construct interacts with RNA transcripts of the target gene to reduce or eliminate expression of the target gene encoding the biological substance, wherein the filamentous fungal strain is an *Aspergillus niger*, an *Aspergillus oryzae*, or a *Trichoderma reesei* strain.

9. The filamentous fungal strain of claim 8, wherein the first homologous region comprises at least 19 nucleotides of the target gene.

10. The filamentous fungal strain of claim 8, wherein the second homologous region comprises at least 19 nucleotides of the first homologous region, wherein at least 19 nucleotides are in reverse order relative to the corresponding region of the first homologous region.

11. The filamentous fungal strain of claim 8, wherein the first and second nucleotide sequences are separated by a third nucleotide sequence.

12. The filamentous fungal strain of claim 11, wherein the third nucleotide sequence comprises at least 5 nucleotides.

13. The filamentous fungal strain of claim 8, wherein expression of the target gene is eliminated.

14. The filamentous fungal strain of claim 8, wherein the interfering RNA interacts with RNA transcripts of one or more homologues of the target gene to reduce or eliminate expression of the one or more homologues of the target gene.

* * * * *